United States Patent [19]
Higgins et al.

[11] Patent Number: 5,830,396
[45] Date of Patent: Nov. 3, 1998

[54] METHOD FOR PROCESSING THERMOPLASTICS, THERMOSETS AND ELASTOMERS

[75] Inventors: Joel C. Higgins, Claypool; Garry Lee England, Winona Lake, both of Ind.

[73] Assignee: Biomet, Inc., Warsaw, Ind.

[21] Appl. No.: 485,888

[22] Filed: Jun. 7, 1995

Related U.S. Application Data

[63] Continuation-in-part of Ser. No. 323,375, Oct. 14, 1994, abandoned, which is a continuation-in-part of Ser. No. 6,747, Jan. 21, 1993, Pat. No. 5,466,530.

[51] Int. Cl.$^6$ ................................................ B29C 43/12
[52] U.S. Cl. ..................... 264/109; 264/120; 264/122; 264/320; 264/DIG. 69
[58] Field of Search ........................... 264/DIG. 69, 120, 264/126, 115, 122, 112, 113, 109, 320; 425/405.2

[56] References Cited

U.S. PATENT DOCUMENTS

| | | | |
|---|---|---|---|
| 4,102,966 | 7/1978 | Duperray et al. | 264/112 |
| 4,187,210 | 2/1980 | Howard, Jr. . | |
| 4,587,163 | 5/1986 | Zachariades . | |
| 4,934,919 | 6/1990 | Matsushita et al. | 425/405.2 |
| 5,030,402 | 7/1991 | Zachariades . | |
| 5,037,928 | 8/1991 | Li et al. . | |
| 5,075,057 | 12/1991 | Hoedl | 264/115 |
| 5,131,834 | 7/1992 | Potter | 425/389 |
| 5,167,889 | 12/1992 | Alvarez et al. | 264/120 |
| 5,210,130 | 5/1993 | Howard, Jr. . | |
| 5,505,984 | 4/1996 | England et al. | 427/2.24 |

FOREIGN PATENT DOCUMENTS

WO/9427651  12/1994  WIPO .

OTHER PUBLICATIONS

Serial No. 08/477,161, Filed Jun. 7, 1995, for Method For Forming Biocompatible Components.

J.R. Davis Davis & Associates, *ASM Materials Engineering Dictionary*, pp. 62, 277.

Bartel, Donald L. et al., "The Effect of Conformity, Thickness, and Material on Stresses in Ultra–High Molecular Weight Components for Total Joint Replacement," *The Journal of Bone and Joint Surgery*, vol. 68–A, No. 7, Sep. 1986, pp. 1041–1051.

Pappas, M.J. et al., "Contact Stresses in Metal–Plastic Total Knee Replacements: A Theoretical and Experimental Study," *Biomedical Engineering Technical Report*. No. 003, Jan. 23, 1986, pp. 1–7.

Bartel, Donald L. et al., "Evaluation and Design of the Articular Surface," pp. 61–72.

Elbert, K.E. et al., "In Vivo Changes in Material Properties of Polyethylene and Their Effects on Stresses Associated with Surface Damage of Polyethylene Components," *34th Annual Meeting, Orthopaedic Research Society*, Feb. 1–4, 1988, Atlanta Georgia.

(List continued on next page.)

*Primary Examiner*—Mary Lynn Theisen
*Attorney, Agent, or Firm*—Harness, Dickey & Pierce, P.L.C.

[57] ABSTRACT

A method for forming products includes the step of forming an incompletely consolidated stock from a powder. A substantially completely consolidated stock is then formed from the incompletely consolidated stock. Finally, the substantially completely consolidated stock is machined to form the final product. The method of the present invention also includes a method for recycling waste thermoplastic materials into useful articles. The method of the present invention also includes a method for processing thermoplastics, thermosets and elastomers. As part of the above, an elastomeric mold may be used, which may be formed from a mandrel.

29 Claims, 15 Drawing Sheets

OTHER PUBLICATIONS

Wright, T.M et al. "Design Considerations for an Acetabular Component Made from an Enhanced form of Ultra High Molecular Weight Polyethylene," *37th Annual Meeting, Orthopaedic Research Society*, Mar. 4–7, 1991 Anaheim, California.

"High Performance Ceramics, the future materials—available today," *ABB Cerama AB* brochure, May 1988.

"Hot Isostatic Pressing: Gets Bigger, Hotter and More Flexible," *Carbide & Tool*, v. 19, No. 2, May–Jun. 1987.

"Automated IsoPress", *ABB Autoclave Systems, Inc.* Technical Bulletin 5319 (pre–Jan. 21, 1992).

Hanes, Hugh D., "Isostatic Pressing: stating the art," *Tooling and Production—Series on basic manufacturing techniques*—No. 5.

"CP3–60: Cold Isostatic Press", ISO–Spectrum Inc. brochure (pre–Jan. 21, 1992).

"HP6–30: Hot Isotatic Press", ISO–Spectrum Inc. brochure (pre–Jan. 21, 1992).

Price, P., and Kohler, S., "Hot Isostatic Pressing of Metal Powders," *Metal Handbook*, pp. 419–443, 1983.

Price, P., and Kolhler, S., "Cold Isostatic Pressing of Metal Powders," *Metal Handbook*, pp. 444–450, 1983.

Hutchings, "Tribology—Friction and Wear of Engineering Materials," *Metalurgy & Materials Science Series*, pp. 14–17, 1992.

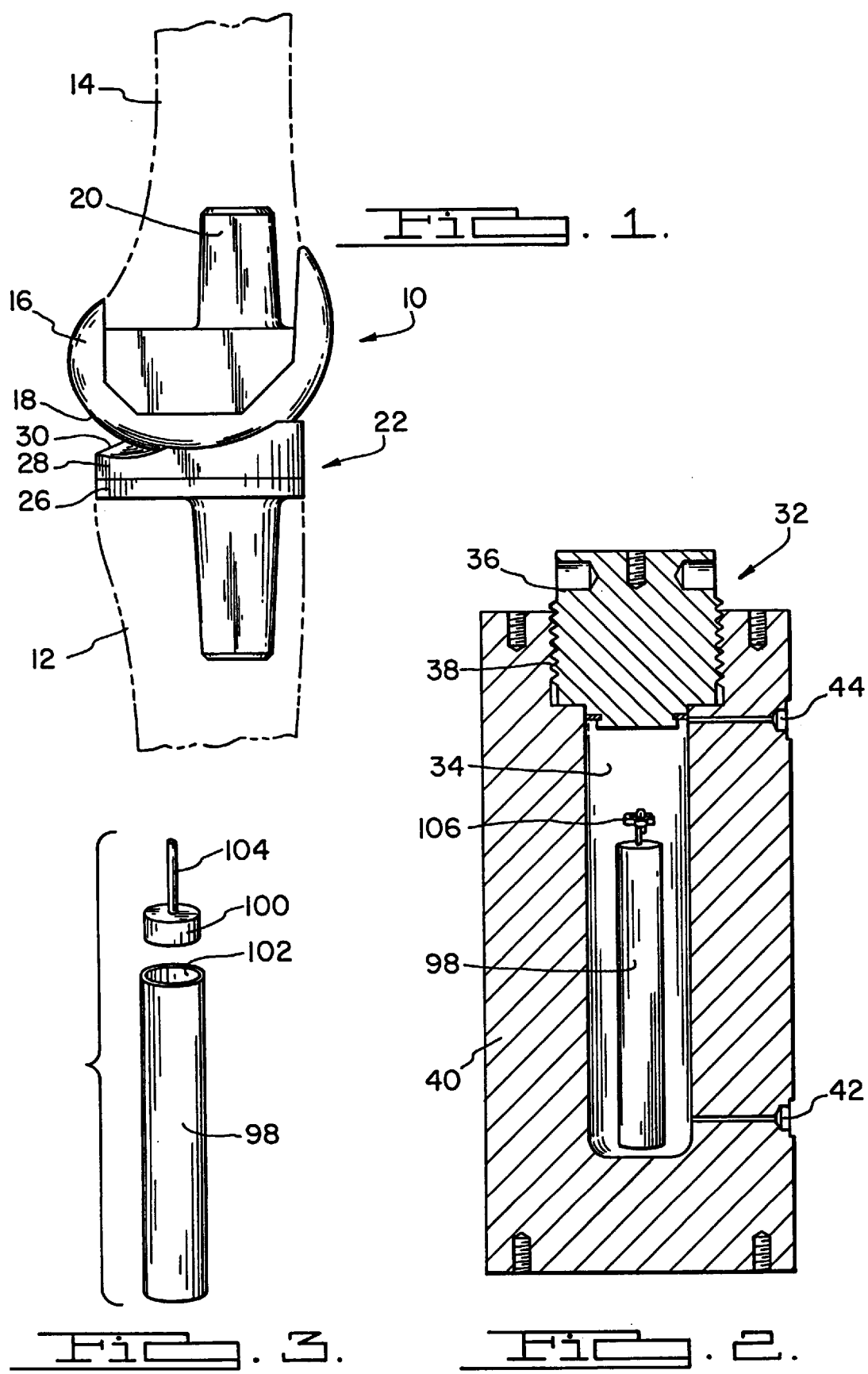

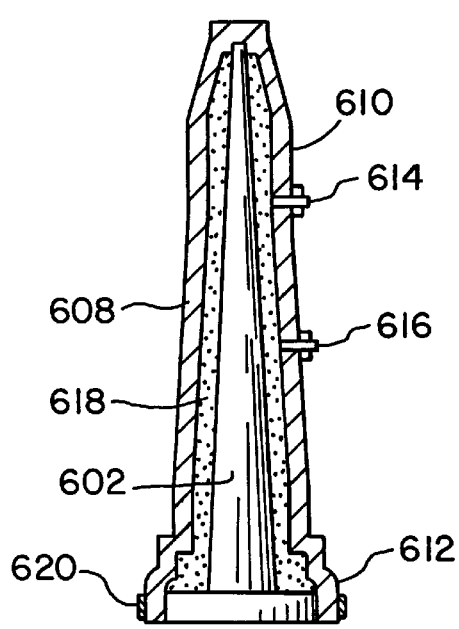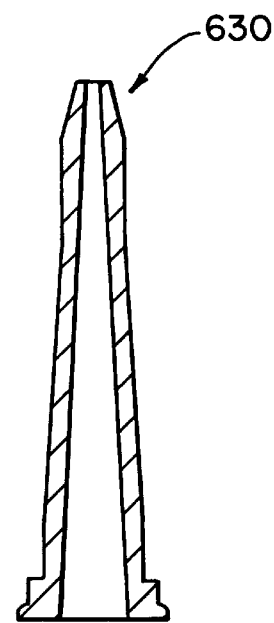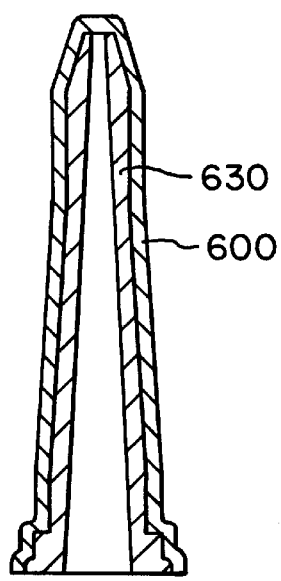

METHOD FOR PROCESSING THERMOPLASTICS, THERMOSETS AND ELASTOMERS

CROSS REFERENCE TO RELATED APPLICATIONS

This is a continuation-in-part of U.S. patent application Ser. No. 08/323,375, filed Oct. 14, 1994, now abandoned, and entitled "METHOD AND APPARATUS FOR RECYCLING THERMOPLASTICS," which is a continuation-in-part of U.S. patent application Ser. No. 08/006,747, filed Jan. 21, 1993, now U.S. Pat. No. 5,466,530, and entitled "METHOD FOR FORMING BIOCOMPATIBLE COMPONENTS."

BACKGROUND OF THE INVENTION

The present invention relates generally to biomedical implant devices, and more particularly to a method for forming biocompatible components.

The present invention also relates generally to processing thermoplastics, thermosets and elastomers and more particularly to a method for forming an article from recyclable thermoplastic, thermoset and elastomeric waste material.

A natural joint in the human body such as a knee joint may undergo degenerative changes due to a variety of etiologies. When these degenerative changes become advanced and are irreversible, it may ultimately become necessary to replace the natural joint with a prosthetic joint. Such a prosthetic joint often includes several biocompatible components which are formed from high strength synthetic materials. These materials are not only able to accommodate the various loading conditions that the prosthetic joint may encounter, but are also biocompatible with the human body. An example of such high strength synthetic materials is ultra-high molecular weight polyethylene which is often used when there is relative movement between the adjacent metallic surface of a prosthetic joint.

Biocompatible components which are made from ultra-high molecular weight polyethylene are often formed using one of two different techniques. In one technique, a relatively precise amount of polyethylene powder is placed between two halves of a die which are then simultaneously compressed and heated. After the powder is densified using standard sintering techniques, the die is allowed to cool. The biocompatible component is then removed from the die and is sterilized in a manner well-known to those skilled in the art.

In the second technique, a substantially completely consolidated polyethylene stock is first formed and then the biocompatible component is machined from the substantially completely consolidated stock. Several methods exist which may be used to form the substantially completely consolidated stock. In one method, the substantially completely consolidated stock is extruded by placing polyethylene powder in a cylindrical chamber having an opening of a particular shape at one end of the chamber. A hydraulically operated piston located at the other end of the cylinder is then used to compress the polyethylene powder. The force exerted by the piston on the polyethylene powder causes the powder to compact. Heat is also applied to solidify the powder as it moves through the cylinder. In another method for forming a substantially completely consolidated stock, polyethylene powder is placed between two flat plates which are compressed while heat is applied. As this occurs, the polyethylene powder is densified so as to form the substantially completely consolidated stock.

While these two techniques for forming biocompatible components are effective, they nevertheless have certain disadvantages. With respect to the first technique described above, it will be appreciated that only one biocompatible component can be made at one time. Accordingly, this technique is relatively inefficient in terms of the amount of time required to make the biocompatible component. With respect to the second technique in which the biocompatible component is formed from a substantially completely consolidated stock, the resulting consolidated stock may often require a stress relief operation or an annealing operation prior to machining. In addition, when polyethylene stock is formed by heating polyethylene powder between two plates acting under pressure, the resulting product may have density gradients or voids due to the relatively nonuniform pressure applied to the powder across the plates.

In addition, methods are also known for treating ultra-high molecular weight polyethylene prior to being machined into a biocompatible component. One such method is disclosed in U.S. Pat. No. 5,037,928. However, during the procedure described in this reference, the polyethylene stock is placed under a sufficient pressure so as to induce pressure crystallization of the stock. This pressure crystallization tends to cause increased susceptibility to wear. In addition, the use of this relatively high pressure required that relatively expensive pressure containment vessels be used. Furthermore, this method describes processing preformed polyethylene stock which often has unwanted density gradients or voids as described above.

In the processing of thermoplastics, thermosets and elastomers, especially waste thermoplastics, thermosets and elastomers, the methods for recycling such materials and the ability to produce useful articles from recyclable materials has been limited. Current methods utilize an extrusion process for compressing granulated thermoplastics into articles whose shape is determined by the shape of the die outlet. As such, articles made through this type of process are limited in their dimensions to articles having a constant cross-section. Further, most extrusion processes require that dirt, metals and other impurities be separated from the thermoplastic material prior to the extrusion process, since extrusion equipment can be damaged by such materials. However, the removal of dirt, metals and other impurities from the thermoplastic material is costly and time consuming. In addition, products made under current processes often have limited usefulness due to insufficient yield stress, tensile stress and elongation.

SUMMARY OF THE INVENTION

An advantage of the present invention is to provide a method for forming biocompatible components using a multiple-step technique which can produce biocompatible components relatively quickly at a reduced cost.

A further advantage of the present invention is to provide a method for forming biocompatible components which produces a stock of consolidated ultra-high molecular weight polyethylene which can be machined without being subjected to a stress relief or annealing operation.

Another advantage of the present invention is to provide a method for forming biocompatible components which does not substantially increase the crystallization of the stock used to form the biocompatible component.

A further advantage of the present invention is to provide a method for forming biocompatible components which uses both a cold isostatic pressure treatment as well as a hot isostatic pressure treatment.

A further advantage of the present invention is to provide a method for forming biocompatible components which enhances the bonding between the composite materials from which the biocompatible component is made.

A further advantage of the present invention is to provide a method for forming biocompatible components which facilitates the adhesion of a porous metal coating.

A further advantage of the present invention is the provision of a method and apparatus for forming articles from recyclable thermoplastic, thermoset and elastomeric waste material whose size may be varied in each of three dimensions.

Another advantage of the present invention is the provision of a method and apparatus for forming articles from recyclable thermoplastic, thermoset and elastomeric waste material which does not require the removal of dirt, metals or other impurities prior to processing.

A further advantage of the present invention is that the method for forming articles from recyclable thermoplastic, thermoset and elastomeric waste material may be practiced based upon standard hydraulic systems that are relatively inexpensive, and are often currently in use at many industrial locations.

Another advantage of the present invention is to manufacture products from waste material that possess increased strength and elongation.

In one form thereof, the present invention provides a method for forming biocompatible components from a powder such as ultra-high molecular weight polyethylene. The method includes enclosing the powder in a first container and subjecting the first container to a cold isostatic pressure treatment which forms an incompletely consolidated stock from the powder. The incompletely consolidated stock is removed from the first container and is placed in a second container which is then located within a hot isostatic press and is subjected to a hot isostatic pressure treatment. The hot isostatic press treatment forms the relatively completely consolidated stock from the incompletely consolidated stock. The relatively completely consolidated stock is then machined into a biocompatible component.

In another form thereof, the present invention provides a method and apparatus for forming an article from recyclable thermoplastic waste material. The method includes providing a ground thermoplastic material, placing the thermoplastic material into a mold, and subjecting the thermoplastic material to an isostatic pressure treatment. This process forms articles that can be sized specifically in each of three dimensions.

In another form thereof, the present invention provides a method and apparatus for forming an article from recyclable thermoplastic, thermoset and elastomeric waste material. The method includes providing ground waste material, mixing a binder with the waste material, placing the waste-binder mixture into a mold, and subjecting the mixture to an isostatic pressure treatment. This process forms articles that can be sized specifically in each of three dimensions.

In another form thereof, the present invention provides a method for forming biocompatible components having substantially final configuration, dimensions and surface texture. The method includes providing an elastomeric mold, which can be formed by dip-forming about a mandrel. A material suitable for pressing during a compression process is then introduced into the elastomeric mold and is subjected to a cold isostatic press treatment, which forms an incompletely consolidated stock. The incompletely consolidated stock is then subjected to a hot isostatic press treatment, either within the elastomeric mold, or within a second container, thereby forming a biocompatible component.

Other advantages and objects of the present invention will become apparent to those skilled in the art from the subsequent detailed description, appended claims and drawings.

BRIEF DESCRIPTION OF THE DRAWINGS

FIG. 2 is a cross-sectional view of a cold isostatic press of the type used in accordance with the teachings of the preferred embodiment of the present invention;

FIG. 3 is a perspective view of the first container used with the cold isostatic press shown in FIG. 2 according to the preferred embodiment of the present invention;

FIG. 16 is a cross-sectional view illustrating an isostatic press suitable for use with the method of the present invention;

FIG. 35 is a cross-sectional view of a isostatic press containing a mandrel and a material suitable for pressing, used for forming a second mandrel according to a preferred embodiment of the present invention;

FIG. 36 is a cross-sectional view of a second mandrel formed according to a preferred embodiment of the present invention; and FIG. 37 is a cross-sectional view of a second mandrel and an sleeve formed thereupon according to a preferred embodiment of the present invention.

DETAILED DESCRIPTION OF THE PREFERRED EMBODIMENT

It should be understood that while this invention is described in connection with a particular example thereof, the scope of the invention need not be so limited. Rather, those skilled in the art will appreciate that the following teachings can be used in a much wider variety of applications than the examples specifically mentioned herein.

Figure 1B:
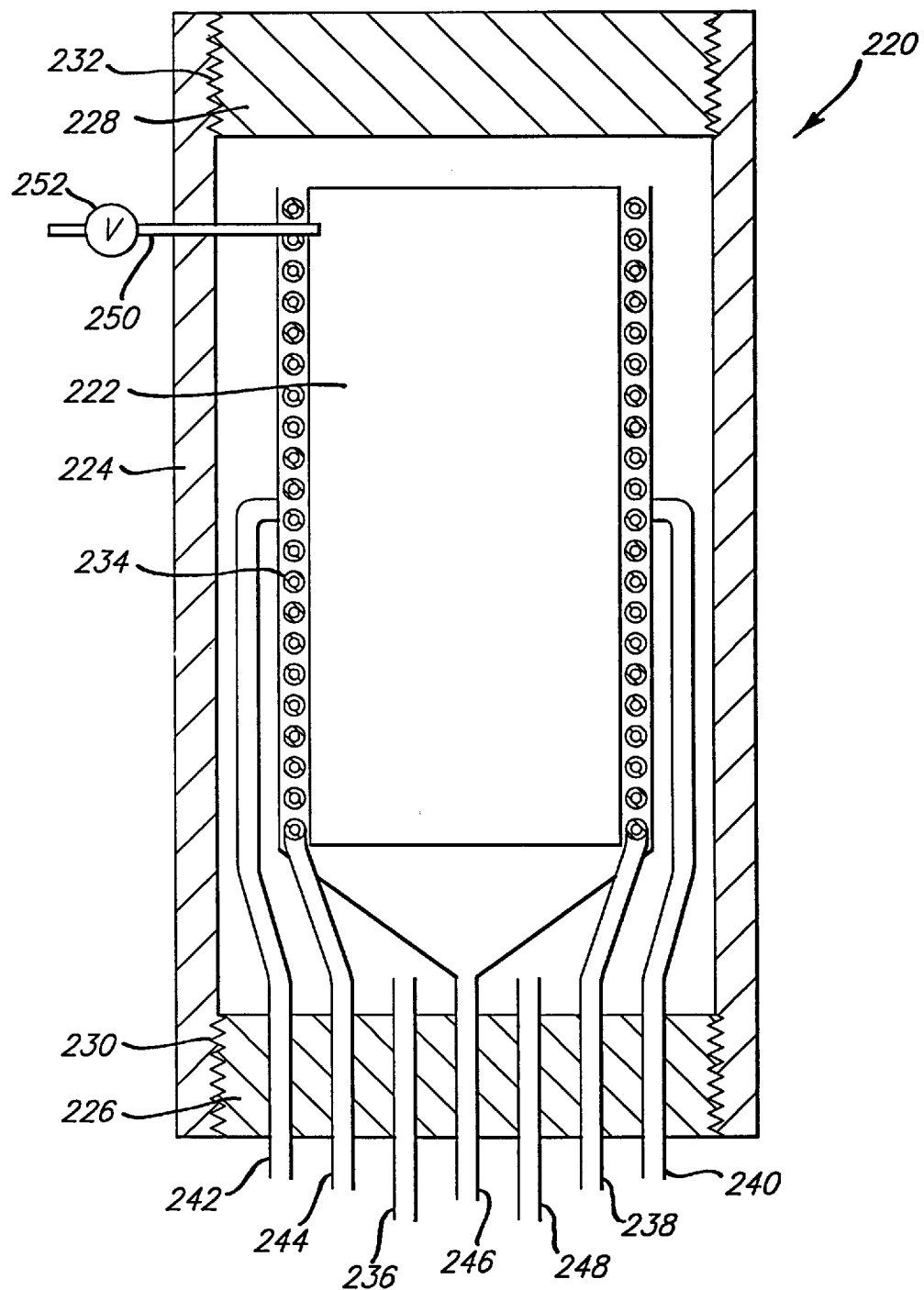
FIG. 1 is a sagittal elevational view of a knee joint prosthesis including a biocompatible component in the form of a tibial bearing formed from ultra-high molecular weight polyethylene by the preferred embodiment of the present invention.

Referring now to FIG. 1, a knee joint prosthesis is shown which is generally designated by the numeral 10. The knee joint prosthesis 10 is functionally depicted as being secured to a tibia 12 and a femur 14 of a surgically resected knee joint, with the tibia 12 and femur 14 being shown in phantom. The knee joint prosthesis 10 is shown to include a femoral component 16 having a bearing surface 18. The femoral component 16 is secured to the femur 14 by means of an inferiorly extending femoral stem 20 inserted into a matching bore created within the femur 14 in a manner well-known to those skilled in the art.

The knee joint prosthesis 10 is further shown to include a tibial component 22 that is secured to the tibia 12 by means of an interiorly extending tibial stem 24 inserted into a matching bore created within the tibia 12 in a similar manner as that described above. The tibial component 22 includes a platform-like tibial tray 26 which is used to support a tibial bearing 28 constructed by the method of the present invention. The tibial bearing 28 is formed to be symmetrically oriented about the sagittal plane. In operation, the tibial bearing 28 provides a bearing surface 30 that is operable to accept a rotatable, low friction contact relationship with the bearing surface 18 of the femoral component 16.

The tibial bearing 28 is formed of a low friction material having enhanced wear resistance properties. In a preferred embodiment, the tibial bearing 28 is machined from a substantially completely consolidated stock that is molded from an ultra-high molecular weight polyethylene powder having a molecular weight of from about 3 million to about 6 million. The ultra-high molecular weight polyethylene powder may be any powder conforming to ASTM F-648, though preferable powders include Hifax 1900 resin available from Himont and GUR 405 or 415 resin available from Hoechst Celanese. It will be understood, however, that other suitable materials may be used to form a stock from which a tibial bearing 28 may be machined. For example, the formation of articles from this method can be accomplished using other polymer materials in powder form, preferably having a molecular weight of from about 3 million to about 6 million. The specific method used to form the tibial bearing 28 includes several steps which are more fully described below. However, several of these steps involve the use of either a cold isostatic press or a hot isostatic press. Accordingly, the structure and operation of the cold isostatic press and the hot isostatic press will now be described.

Referring to FIG. 2, a cold isostatic press 32 according to the preferred embodiment of the present invention is shown which includes a pressure chamber 34 that has an upper cover 36. The upper cover 36 includes a threaded closure 38 that enhances a sealed condition within the pressure chamber 34 when the pressure chamber 34 is pressurized. When the pressure chamber 34 is sealed in this manner, the length of the pressure chamber 34 is approximately 24–30 inches and the diameter of the pressure chamber 34 is approximately 12 inches. The pressure chamber 34 is substantially surrounded by an annular wall 40 which is operable to define the pressure chamber 34, and has a thickness which is sufficient to contain the pressure within the pressure chamber 34.

The cold isostatic press 32 further includes a pressure inlet line 42 and a pressure relief line 44. The pressure inlet line 42 and pressure relief line 44 are preferably tubular passageways each regulated by a pressure control mechanism (not shown) that are operable to accommodate a pressurized transfer of a gas or liquid fluid from an external source (not shown) into and out of the pressure chamber 34.

The cold isostatic press 32 is preferably designed to operate at pressures capable of compacting the powder to about 60–80% of its desired final density, with the preferable range being between 65–75%. The cold isostatic press 32 may be that which is available from National Forge, Andover, Massachusetts, or Models IP6-24-60 and IP8-36-60 which are available from ABB Autoclave Systems, Inc. of Columbus, Ohio. However, other suitable cold isostatic presses may be used.

The hot isostatic press 46 will now be described with reference to FIG. 3. The hot isostatic press 46 is shown to include a pressure chamber 48 which is defined in part by an annular wall 50, the thickness of which is between about 6 inches and about 3 inches. In addition, the pressure chamber 48 is about 18 inches in diameter and is about 53 inches in length. The hot isostatic press 46 further includes a lower closure 52 and upper closure 54 which are threadedly attached to the annular wall 50 by matching buttress threads 56 and 58. It is to be understood, however, that a pin locking mechanism may also be employed for securing the lower closure 52 and upper closure 54 to the annular wall 50. The lower closure 52 and upper closure 54 are operable to maintain a heated and pressurized condition within the pressure chamber 48 during the hot isostatic pressure treatment described below.

The hot isostatic press 46 further includes a plurality of heating elements 60 that are operable to generate thermal energy within the pressure chamber 48. Alternatively, the hot isostatic press 46 may include another heating means, such as a solution jacket adjacent to the pressure chamber 48, that is operable to contain a hot fluid for providing thermal energy to the pressure chamber 48. The hot isostatic press 46 is also shown to include a cooling jacket 62 which comprises a plurality of coils encircling the annular wall 50. The cooling jacket 62 is operable to contain a suitable heat transfer fluid for removing thermal energy from the hot isostatic press 46 by a transfer of thermal energy into the cooling fluid. It will be understood, however, that the cooling function accomplished by the cooling jacket 62 can be performed by another cooling means disposed at a different location within the hot isostatic press 46, such as within the pressure chamber 48 or between the pressure chamber 48 and the annular wall 50.

The hot isostatic press 46 further includes a heat shield 64 which is located between the annular wall 50 and the heating elements 60. The heat shield 64 is operable to limit heat losses from within the pressure chamber 48 and to assist in controlling the temperature within the pressure chamber 48. The hot isostatic press 46 also includes a pressure system (not shown) of a type well-known to those skilled in the art that is operable to pressurize the pressure chamber 48. The pressure system also communicates with the pressure chamber 48 by means of a pressure input/output line 68 that is connected to an inert gas source and compressor of a type well-known to those skilled in the art. In a preferred embodiment, the inert gas is argon, though nitrogen, helium and neon gases may also be used.

The hot isostatic press 46 further includes a power distribution system (not shown) of a type well-known to those skilled in the art. The power distribution system is used for controlling the heat and pressure within the pressure chamber 48. In addition, the electrical energy required by the heating elements 60 is provided in this embodiment by an electrical power line 72 that is connected to an electrical power source (not shown).

The hot isostatic press 46 is operable to change the temperature within the pressure chamber 48 from an initial room temperature of from about 60° F. to about 70° F. to an operating temperature of from about 365° F. to about 420° F. In addition, the hot isostatic press 46 is also operable to change the pressure within the pressure chamber 48 from approximately atmospheric pressure to an operating pressure of preferably from about 7,500 pounds per square inch to about 10,000 pounds per square inch. The hot isostatic press 46 may be one of several well-known to those skilled in the art, such as Model HP6-30, available from Iso-Spectrum, Inc. of Columbus, Ohio. Other suitable hot isostatic presses are available from National Forge of Andover, Massachusetts. However, other suitable hot isostatic presses may be used.

Figure 4:
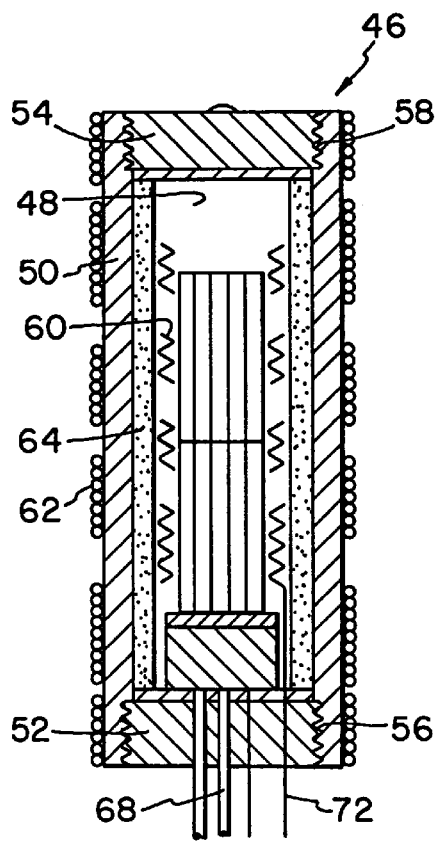
FIG. 4 is a cross-sectional view of a hot isostatic press of the type used in accordance with the teachings of the preferred embodiment of the present invention.

The method of the preferred embodiment of the present invention will now be described with reference to FIG. 4 which comprises the steps 80 through 96. At step 80, an ultra-high molecular weight polyethylene powder is introduced into a first container 98 (see FIG. 3) so as to substantially fill the first container 98. The first container 98 is preferably both flexible and collapsible, and is made from a material that has sufficient strength to contain the powder over the operating pressure ranges during the cold isostatic pressure treatment without exhibiting any physical deterioration, chemical degradation or chemical interaction with the powder disposed therein. It is also preferred that the first container 98 be made of a material that will not adhere to the powder at any time during the cold isostatic pressure treatment.

In a preferred embodiment, the first container 98 is a cylindrical polyurethane container of dimensions approximately 6 inches in diameter, 18 inches in length, and has a wall thickness of approximately one-half inch to three-fourths inch. The first container 98 is sealed by means of a plug 100 that is inserted into a matching port 102 at one end of the first container 98. The plug 100 is secured to the first container 98 by means of an adhesive, such as a hot melt glue, located on the top of the interface of the plug 100 and the matching port 102. Because it is desirable that the first container 98 be substantially evacuated prior to the cold isostatic pressure treatment, the plug 100 of the first container 98 preferably includes an evacuation/de-airing tube 104. The evacuation/de-airing tube 104 is operable to be connected to an evacuation pump (not shown) and subsequently sealed by any suitable means prior to the cold isostatic pressure treatment.

It will be noted that the size and shape of the first container 98 will vary depending upon the desired size and shape of the consolidated stock being formed. It will also be noted that other suitable materials may be used to form the first container 98 and that other suitable means may be used for substantially sealing and evacuating the first container 98. For example, a flexible and collapsible rubber material may be employed for constructing the first container 98. When constructed of polyurethane, the first container 98 may be reused provided it is not subjected to extended periods of high temperature.

Once the first container 98 has been filled with powder, the first container 98 is sealed in the manner described above. The first container 98 is then substantially evacuated and then the evacuation/de-airing tube 104 is sealed by any suitable means such as by a clamp 106. As is illustrated by the step 82, the first container 98 is then located within the pressure chamber 34 of the cold isostatic press 32. The pressure chamber 34 is substantially sealed at step 84 to enclose the first container 98 by threading the upper cover 36 onto the matching threads 38 disposed upon the annular wall 40.

The first container 98 is then subjected to a cold isostatic pressure treatment as indicated by the step 86 during which a uniform pressure is applied to the first container 98. In this regard, the pressure applied to the first container 98 is developed by introducing a pressurized fluid into the pressure chamber 34. This pressurized fluid may be water, mineral oil or other oils having similar compressive properties, as well as inert gases such as argon, nitrogen, helium and neon. In addition, the pressure chamber 34 may be partially filled with water while the pressurized gas may be used to fill the remainder of the pressure chamber 34. The pressure within the pressure chamber 34 is preferably increased as quickly as possible from approximately atmospheric pressure to a pressure sufficient to form the powder into an incompletely consolidated stock that can be manipulable for further processing without substantial degradation. Suitable maximum pressures range from 1100 psi to 10,000 psi which are generally sufficient to compact the powder to 60–80% of its final density. Below this range the incompletely consolidated stock is structurally unstable and above this range gases may become trapped within the incompletely consolidated stock during evacuation of the first container 98. In a preferred embodiment, the maximum pressure applied to the first container 98 is approximately 1500 psi, and the typical length of time for increasing the pressure to this level may be approximately 2 to 5 minutes. However, maximum pressure applied to the first container 98 is dependent upon several factors including the size of the first container 98, the amount of powder within the first container 98, the size of the resulting stock needed to manufacture the tibial bearing 28 and the size of the pressure chamber 34. The pressure is preferably held at the maximum pressure for approximately one minute, though longer times can be used.

After the maximum pressure within the cold isostatic press 32 is maintained for approximately one minute, the pressure is slowly reduced so as to allow the resulting incompletely consolidated stock to relax within the first container 98 without yielding to outward internal pressure which can cause the incompletely consolidated stock to lose integrity. The pressure is preferably released over a period of from approximately 10 to approximately 30 minutes, although longer times can be used.

The cold isostatic press treatment enhances a uniform density within the incompletely consolidated stock and reduces internal stresses from appearing within the material being formed during the subsequent hot isostatic pressure treatment. In addition, the shape of the incompletely consolidated stock is in large part dependent upon the shape of the first container 98. The incompletely consolidated stock resulting from the cold isostatic press treatment is typically compacted to a preferred density of about 70% of its desired final density following the hot isostatic pressure treatment.

Figure 5:
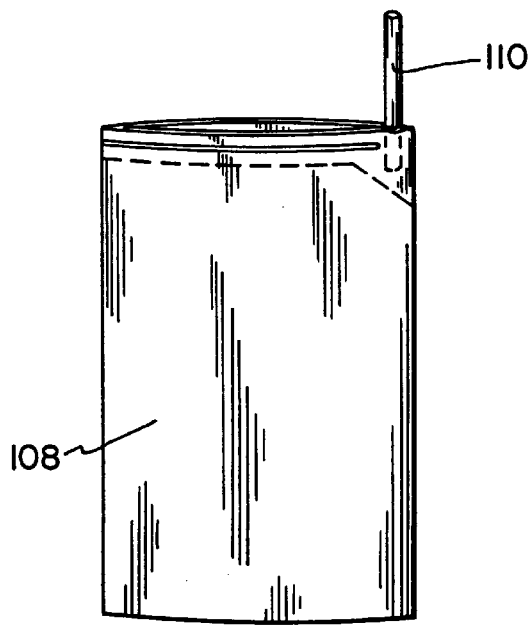
FIG. 5 of the second container used in conjunction with the hot isostatic press shown in FIG. 4 according to the preferred embodiment of the present invention.
Figure 6:
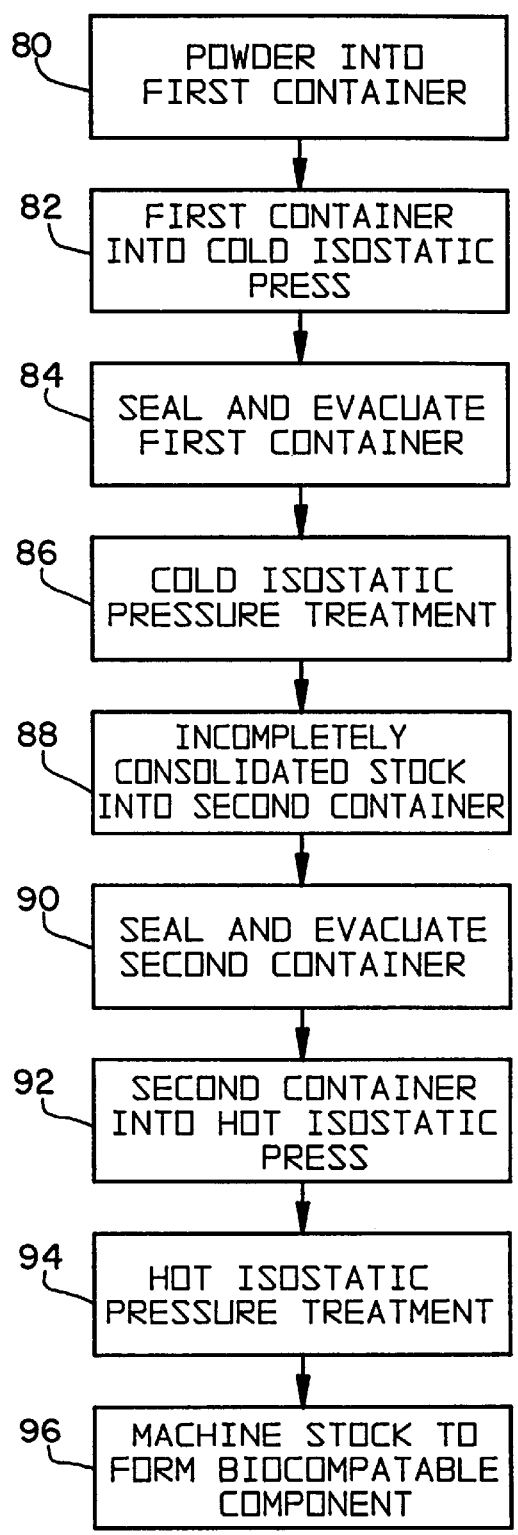
FIG. 6 is a flow diagram illustrating the steps for forming a biocompatible component according to the preferred embodiment of the present invention.

After the incompletely consolidated stock has been removed from the first container 98, the incompletely consolidated stock is placed in a second container 108 (see FIG. 5) as indicated by the step 88. The second container 108 is preferably a collapsible container made from a material that has sufficient strength to contain the incompletely consolidated stock over the temperature and pressure ranges encountered in the hot isostatic press treatment without exhibiting any physical deterioration, chemical degradation or chemical interaction with the incompletely consolidated stock. It is also preferred that the second container 108 be made of a material that will not adhere to the incompletely consolidated stock at any time during the hot isostatic pressure treatment. In a preferred embodiment, the second container 108 is a foilized heat sealable bag that has an external surface formed from a layer of an aluminum foil with a polyester vapor barrier, and has an internal surface formed from a heat-sealable, low density polyethylene layer on its internal surface. The second container 108 may typically be approximately 18 inches in length, approximately 12 inches in width and have a wall thickness of between approximately 2–3 mils. As will be appreciated by those skilled in the art, the second container 108 may be made from other suitable materials as well.

Because it is desirable to have the second container 108 be substantially evacuated prior to the hot isostatic pressure treatment, the second container 108 preferably includes an evacuation tube 110 that is operable to be connected to a vacuum pump (not shown). In this regard, the evacuation tube 110 is placed in the second container 108 and then a heat sealer is used to seal that region of the second container 108 which is not immediately adjacent to the evacuation tube 110. Hot melt glue is then placed around the region of the second container 108 which is adjacent to the evacuation tube 110.

It will be noted that the size and shape of the second container 108 will vary depending upon the desired size and shape of the consolidated stock being formed. It will also be noted that other suitable materials may be used for the second container 108 and that other suitable means may be used for sealing and evacuating the second container 108.

After the incompletely consolidated stock is placed in the second container 108, the second container 108 is evacuated in similar fashion to the evacuation of the first container 98 as indicated by the step 90. A heat sealer is then used to substantially enclose the second container 108 at a region below the evacuation tube 110. The evacuation tube 110 may then be removed from the second container 108.

Once the incompletely consolidated stock is placed within the second container 108 and the second container 108 is sealed and evacuated. The second container 108 is then placed into the pressure chamber 48 of the hot isostatic press 46 as indicated by the step 92 of the present invention. The lower closure 52 and the upper closure 54 of the hot isostatic press 46 are then closed to substantially enclose the second container 108 within the hot isostatic press 46.

At step 94, the incompletely consolidated stock undergoes the hot isostatic pressure treatment. In this regard, the pressure within the pressure chamber 48 is initially raised to approximately 24 psi while the temperature of the hot isostatic press 46 is raised between 365° F. and 420° F. Below this range the incompletely consolidate stock does not melt and above this range the polyethylene may degrade. Preferably, the temperature of the hot isostatic press is raised to between 365°–385° F. to minimize the possibility that degradation will occur. Most preferably, the temperature is raised to 365° F. Once 365° C. is reached, the temperature of the hot isostatic press 46 is raised as quickly as possible and may typically heat between one to three hours.

When the temperature of the hot isostatic press 46 reaches approximately 365° C., the pressure within the pressure vessel 46 is also increased over a 1–2 hours period to a pressure preferably between about 7,500 to about 10,000 psi. It will be appreciated that the maximum pressure may range from about 3,000 psi to about 40,000 psi. However, pressures below 3,000 psi or above 40,000 psi tend to cause consolidation errors to occur or may cause the resulting completely consolidated stock to have an undesirable crystalline structure. The preferred maximum pressure between 7,500 psi and 10,000 psi is dependent upon several factors including the size, shape and construction of the second container, the dimensions of the pressure chamber 48 and the desired final diameter of the resulting completely consolidated stock. In addition, the duration of the hot isostatic pressure treatment may also depend on the size of the resulting completely consolidated stock. For example, smaller diameters of the completely consolidated stock (e.g., 1-½ inches) typically require less time to become fully compacted, while larger diameters of completely consolidated stock, such as 4 inches, typically require more time to become fully cured. In addition, the use of the lowest satisfactory pressure is desirable as it would tend to prolong equipment life. An inert gas such as argon is preferably used in the hot isostatic press 46 as the pressure medium. Alternative selections for the pressure medium include nitrogen, helium and neon gases, although these gases can be chemically reactive under certain conditions.

Once the temperature and pressure have reached the desired levels, the temperature and pressure of the pressure chamber 48 remains relatively constant for a given dwell time. During this dwell time, the powder is further compressed so as to minimize any compression release that may occur following termination of the application of heat and pressure. Preferred dwell times are dependent upon the desired final diameter of the consolidated stock being produced, and range from approximately 45 minutes to several hours or more. For example, typical desired dwell times may be approximately 45 minutes to approximately 1 hour for a 1 inch diameter consolidated stock, approximately 2 hours for a 2-½ inch diameter consolidated stock, and approximately 5 hours for a 4 inch diameter consolidated stock.

After the second container 108 has been subjected to the desired temperature and pressure for the given dwell time, the hot isostatic press 46 is allowed to cool to room temperature. After the temperature of the hot isostatic press 46 cools to approximately 100° F., the pressure within the pressure chamber 48 is gradually decreased to approximately atmospheric pressure over a period of time that is dependent upon the desired final diameter of the consolidated stock being produced. In this regard, the pressure for larger diameters of consolidated stock may be reduced more slowly because they may typically have a larger internal compression and larger potential energy that are more likely to release upon removal of pressure. For example, a 1 hour pressure release time is preferred for a 4 inch diameter consolidated stock, while a 20 minute pressure release time may be sufficient for a 1-½ inch diameter consolidated stock. After the release time has elapsed, the pressure chamber 48 is then opened and the second container 108 is removed from the pressure chamber 48.

The consolidated stock is removed from the second container 108 and is machined at step 96 under methods well-known to those skilled in the art to produce the desired product, such as the tibial bearing 28, acetabular cup replacement or other biocompatible component. After machining the consolidated stock at step 92 to form the tibial bearing 28, the tibial bearing 28 is then sterilized in a manner well-known to those skilled in the art.

Figure 7:
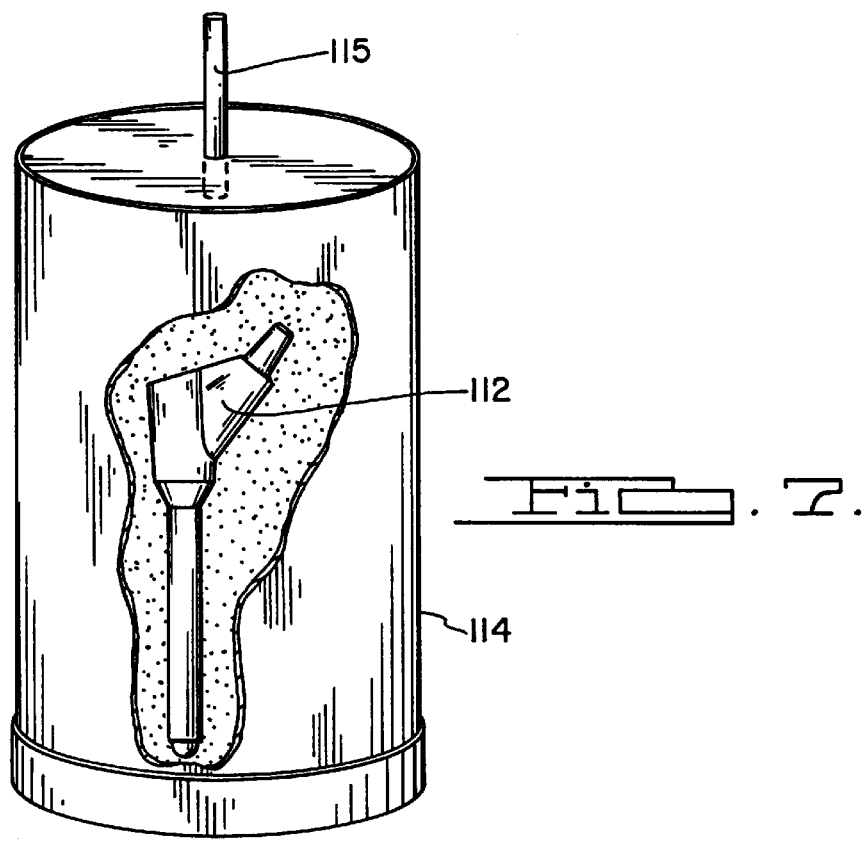
FIG. 7 is a perspective view of the container which is used in accordance with the preferred embodiment of the present invention to enhance binding of the layers of composite material of a biocompatible component.

In addition to using of the hot isostatic press 46 in forming a completely consolidated stock, the hot isostatic press 46 may be also used to enhance the adhesion between materials which form a composite biocompatible component. For example, as shown in FIG. 7, a biocompatible component 112 representing a femoral hip stem of a hip joint prosthesis is shown. The biocompatible component 112 is preferably formed of a biocompatible thermoplastic having a biocompatible fibrous material disposed therein. The biocompatible thermoplastic may be polysulfone, poly ether ketone (PEEK), or poly aryl ether ketone (PAEK), though other suitable materials may be used. The amount and orientation of the biocompatible fibrous material within the biocompatible component 112 is selected to achieve the desired structural modulus for the biocompatible component. The biocompatible fibrous material may be either continuous or chopped fibers, though other suitable materials may be used.

When used in this manner, a sheet of the biocompatible thermoplastic such as polysulfone is first formed into two portions, each portion having a shape generally corresponding to one-half of the biocompatible component 112. Each portion of the biocompatible thermoplastic is then placed within the container 114 with the biocompatible fibrous material disposed between the portions. The container 114 is preferably made from copper or stainless steel. However, other suitable materials such as high temperature silicon, which does adhere to the polysulfone, may also be used. The container 114 is then filled with zirconium oxide beads (i.e., $Zr_2O_3$) and is then evacuated using the evacuation tube 115 which is then sealed. It will be appreciated that zirconium oxide beads do not have to be used when the container 114 is made from a very pliable material such as high temperature silicon. The container 114 is then placed in the hot isostatic press 46 and is subjected to the hot isostatic pressure treatment in a manner similar to that described above. In this regard, the maximum temperature of the isostatic pressure treatment is preferably slightly above the melting temperature of the biocompatible thermoplastic. In addition, the pressure applied and the duration of the hot isostatic pressure treatment should be sufficient to cause the biocompatible thermoplastic to encapsulate the biocompatible fibrous material. Preferably, the temperature will fall within the range of 400°–440° F. while the pressure will be greater than between 5000 psi and 7500 psi, and most preferably greater than 7500 psi. It will be understood by those skilled in the art, however, that the temperature, pressure and duration of the hot isostatic pressure treatment will depend upon the specific materials being used.

Figure 8:
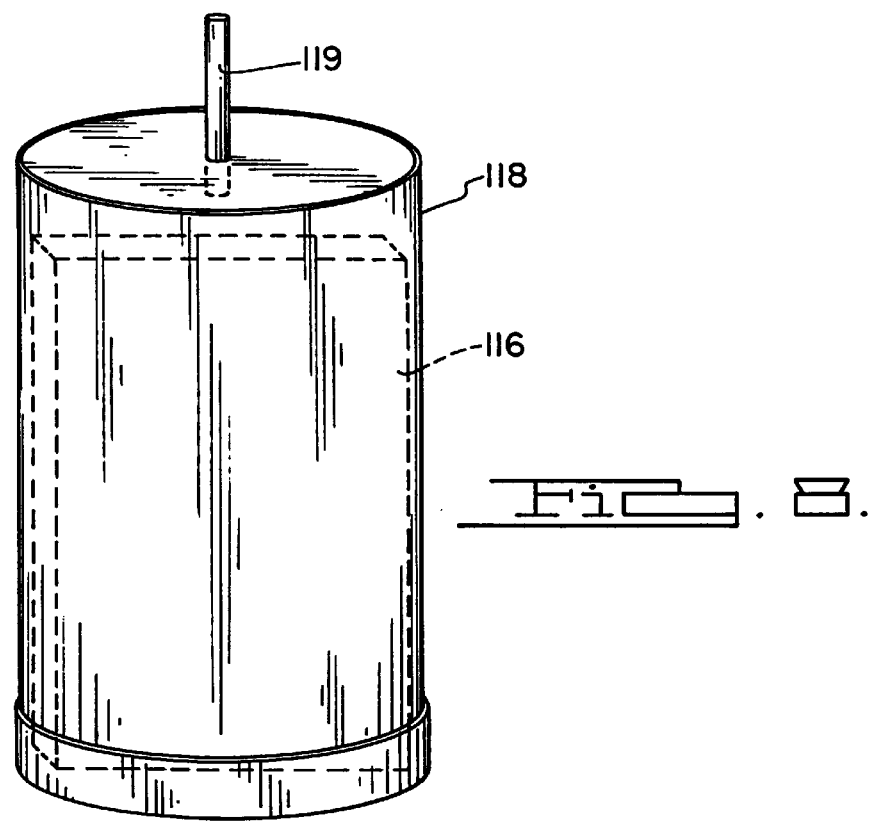
FIG. 8 is a perspective view of the container used in accordance with the preferred embodiment of the present invention to reduce voids in a stock of biocompatible composite material.

The isostatic press 46 may also be used to reduce the voids in a stock of biocompatible composite material prior to being machined into a biocompatible component. For example, as shown in FIG. 8, a biocompatible material stock 116 is shown as being disposed within a container 118. The biocompatible material stock 116 may be made from polysulfone, poly ether ether ketone (PEEK), or poly arly ether ketone (PAEK), though other suitable materials may be used. The container 118 may be a stainless steel or a copper container. However, the container may also be a stainless steel heat treat bag of the type which is available from Sentry Company, Foxboro, Massachusetts, other suitable containers may be used.

When used in this manner, the biocompatible material stock 116 is first placed within the container 118 and then the container 118 is filled with zirconium oxide beads. It will be appreciated, however, that zirconium oxide beads do not have to be used if the container 118 is made from a pliable material such as a heat treat bag. The container 118 is then sealed. A vacuum is then drawn on the container 118 through the evacuation tube 119 and then the evacuation tube 119 is then sealed by closing a valve connected to the evacuation tube 119. The container 118, with the biocompatible stock material 116 located therein, is placed in the isostatic press 46 and the temperature and pressure of the isostatic press 46 are raised to such an extent that the voids formed within the biocompatible stock material 116 are reduced. This reduction in voids occurs because of the external pressure applied to the exterior of the container 118. By using the isostatic press 46 in this manner, the resulting biocompatible material has improved consolidation. The temperature to which the hot isostatic press 46 is raised will be substantially that of the glass transition temperature of the resin of the biocompatible stock material 116, while the pressure applied by the hot isostatic press 46 is as high as reasonably possible. Preferably, the temperature will fall within the range of 400°–440° F. while the pressure will be greater than between 5000 psi and 7500 psi, and most preferably greater than 7500 psi. However, other suitable temperatures and pressures may be used.

Figure 9:
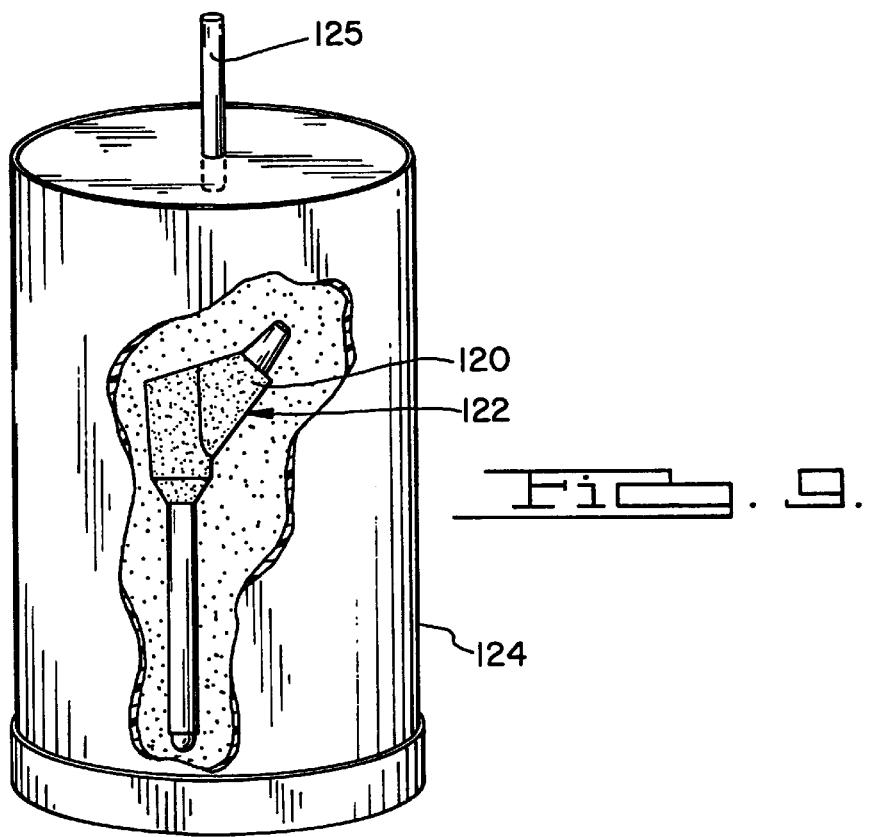
FIG. 9 is a perspective view of the container used in accordance with the preferred embodiment of the present invention to enhance adhesion of a porous coating to a biocompatible component.

The isostatic press 46 may also be used to enhance the adhesion of a porous coating on a biocompatible component formed from a composite material. As shown in FIG. 9, the biocompatible component 120 includes a porous coated surface 122 which is used to facilitate adhesion of the biocompatible component immediately after surgery. The porous coated surface 122 may be applied by a plasma spray operation and may comprise an alloy of Ti-6Al-4V, commercially pure titanium, a cobalt chrome alloy or other biocompatible materials.

When the isostatic press 46 is used to enhance adhesion of a porous coating 122 onto the biocompatible component 120, the porous coated surface 122 is first applied to the biocompatible component 120 by a plasma spray operation. The biocompatible component 120 is then placed in a container 124 and then the container 124 is filled with zirconium oxide beads. The container 124 is then sealed and then is evacuated through the evacuation tube 125. The container 124 is preferably made of stainless steel or copper. However, other suitable materials such as high temperature silicon, which does not adhere to the component 120 may also be used. It will be appreciated, however, that zirconium oxide beads do not have to be used if the container 124 is made from a pliable material such as high temperature silicon. The container 124, with the biocompatible component 120 inside, is then placed in a hot isostatic press 46 which is then operated in a manner similar to that described above. Preferably, the temperature will fall within the range of 400°–440° F. while the pressure will be greater than between 5000 psi and 7500 psi, and most preferably greater than 7500 psi. As a result, the adhesion of the porous coated surface 122 to the biocompatible component 120 is improved.

Figure 10:
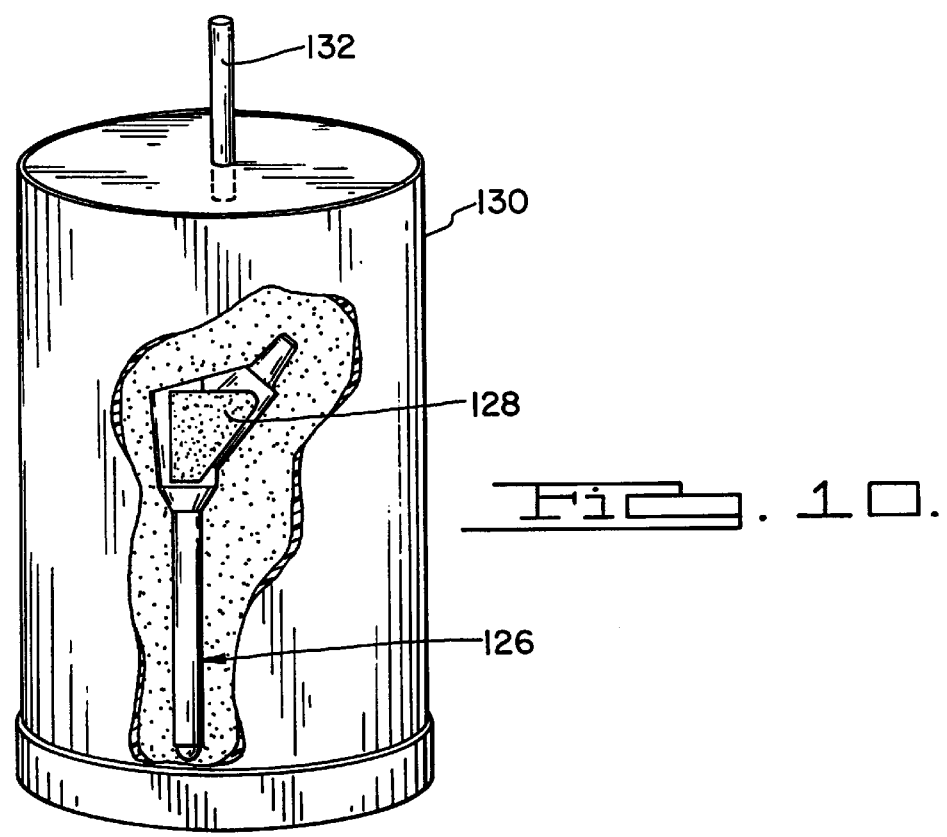
FIG. 10 is a perspective view of the container used in accordance with the preferred embodiment of the present invention to facilitate adhesion of porous coated pads on a biocompatible component.

The hot isostatic press 46 may also be used to enhance adhesion of porous coated pads on a biocompatible component. As shown in FIG. 10, the biocompatible component 126 includes a plurality of porous coated pads 128 which are used to facilitate fixation of the biocompatible component 126 immediately after surgery. The porous coated pads 128 may be made from a titanium alloy such as Ti-6Al-4V, commercially pure titanium, a cobalt chrome alloy or other biocompatible metal alloys. While the porous coating on the porous coated pads 128 may be applied by a flame spray, plasma spray or sputtering techniques, it will be appreciated that other suitable methods may be used.

When the hot isostatic press 46 are used to enhance adhesion of the porous coated pads 128 onto the biocompatible component 126, the regions on the biocompatible component 126 where the porous coated pads 128 are to be placed are first coated with methylene chloride to partially dissolve those regions at the biocompatible component 126. The porous coated pads 128 are then applied to the biocompatible component 126 and are temporarily secured thereto. The biocompatible component 126, together with the porous coated pads 128, are then placed in the container 130 and then the container 130 is filled with zirconium oxide beads. The container may be made from stainless steel or copper, though other suitable materials may be used. In this regard, pliable materials such as high temperature silicon which is able to withstand the operating temperatures and pressures may be used which do not necessarily require the use of zirconium oxide beads. After the container 130 is evacuated through the evacuation tube 132 and the evacuation tube 132 is sealed, the container 130 is placed in the hot isostatic press 46 which is then operated in a manner similar to that described above. Preferably, the temperature will fall within the range of 400°–440° F. while the pressure will be greater than between 5000 psi and 7500 psi, and most preferably greater than 7500 psi. As a result, the porous coated pads 128 are relatively securely attached to the biocompatible component 126.

The principles of the present invention described broadly above will now be described with reference to the following specific example, without intending to restrict the scope of the present invention.

EXAMPLE 1

Polyethylene powder having a molecular weight of approximately 3 million and conforming to ASTM F 648-84 is introduced into a first container formed from polyurethane of approximately 6 inches in diameter, 18 inches in length, and of approximately one-half inch wall thickness. The first container is substantially sealed and substantially evacuated, and is then placed in the cold isostatic press 32. The cold isostatic press is then closed, and the pressure therein is increased by introducing pressurized water into the pressure vessel to approximately 1500 psi over approximately a 2 minute period. The pressure is then maintained within the cold isostatic press for approximately 1 minute, and is then decreased to atmospheric pressure over approximately a 10 minute period. The cold isostatic press is then opened and the first container is removed and opened to reveal a cylindrical incompletely consolidated stock of dimensions 5½ inches in diameter and 14 inches in length.

The incompletely consolidated stock is then placed in a second container. The second container is formed from an aluminum foil layer with a polyester vapor barrier on its external surface and a heat-sealable, low density polyethylene layer on its internal surface. In addition, the second container is approximately 18 inches in length, 12 inches in width and has a wall thickness of 2–3 mils. The second container is then evacuated and sealed. The second container is then placed in the hot isostatic press and then the hot isostatic press is closed.

The temperature of the hot isostatic press is then increased from room temperature to 400° F. over approximately a 1 hour period. At the same time, pressurized argon gas is introduced into the pressure chamber of the hot isostatic press to increase the internal pressure from atmospheric pressure to 10,000 pounds per square inch over approximately a 3 hour period. After reaching 400° F. and 10,000 psi, the temperature and pressure within the hot isostatic press are maintained for approximately 5 hours. The temperature is then allowed to decrease to 100° F. over approximately a 4 hour period. At the same time, the pressure within the hot isostatic press is decreased to atmospheric pressure over a 30 minute period. After release of the pressure and cooling to room temperature, the hot isostatic press is opened and the second container is removed. The second container is then opened to reveal a relatively completely consolidated stock which resembles a cylinder having dimensions of 4 inches in diameter and 12 inches in length. The relatively completely consolidated stock is tested to have a crystallinity of 45%–60%. The consolidated stock is subsequently machined to form a tibial bearing which is then packaged and then exposed 2.5 megarads of radiation from a cobalt source for sterilization.

EXAMPLE 2

Two portions of polysulfone approximately 5 mils in thickness are vacuum formed into a shape which resembles each half of a biocompatible component in the form of a hip joint prosthesis described above. Each portion of the polysulfone representing the halves of the biocompatible component is then placed in a stainless steel container with continuous carbon fibers disposed between the portions. The container is placed in the hot isostatic press and then the hot isostatic press is closed. The temperature of the hot isostatic press is then increased from room temperature to approximately 410° F. over approximately a one hour period. At the same time, pressurized argon gas is introduced into the pressure chamber of the hot isostatic press to increase the internal pressure from atmospheric pressure to 7500 psi over approximately a three-hour period.

After reaching 410° F. and 7500 psi, the temperature and pressure within the hot isostatic press are maintained for approximately a thirty minute period. The temperature is then allowed to decrease to room temperature after which the pressure is released. After the pressure has been released and the hot isostatic press has been cooled to room temperature, the hot isostatic press is opened and the container is removed. The container is then opened to reveal a biocompatible component in which the polysulfone has encapsulated the carbon fibers.

EXAMPLE 3

A biocompatible component in the form of a hip joint prosthesis described above is initially formed from continuous carbon fibers which are encapsulated by polysulfone. Methylene chloride is applied to the upper portion of the biocompatible component so as to partially dissolve the polysulfone. After portions of the polysulfone have been melted, a plurality of porous coated pads described above are applied to the region of the biocompatible component to which methylene chloride is applied. The biocompatible component with the porous coated pads attached is then placed in a stainless steel container of the type described above which is then filled with zirconium oxide beads. After the container is evacuated and sealed, the container is placed in a hot isostatic press and then the hot isostatic press is closed.

The temperature of the hot isostatic press is then increased from room temperature to approximately 410° F. over approximately a one hour period. At the same time, pressurized argon gas is introduced into the pressure chamber of the hot isostatic press to increase the internal pressure from atmospheric pressure to 5000 psi over an approximately a one hour period. After reaching 410° F. and 5000 psi, the temperature in the pressure of hot isostatic press are maintained for approximately 45 minutes. The pressure is then allowed to decrease over approximately a four-hour period, while the temperature within the hot isostatic press is decreased to ambient over a thirty minute period. After release of the pressure and cooling to room temperature, the hot isostatic press is open and the container is removed. The second container is then opened to reveal the biocompatible component with the porous coated pads relatively securely attached.

EXAMPLE 4

A biocompatible material stock in the form of a slab is placed within a stainless steel container which is then formed with zirconium oxide beads. The slab is approximately 1.5 inches thick and is 10 in length and 10 in width. After the container is then evacuated and sealed in the manner described above, the container together with the biocompatible material stock is placed in a hot isostatic press. The temperature of the hot isostatic press is then increased from room temperature to approximately 430° F. over approximately a 0.75 hour time period. At the same time, pressurized argon gas is introduced into the hot isostatic press to increase the internal pressure from atmospheric to approximately 7500 psi over approximately a one hour time period.

After reaching 430° F. and 7500 psi, the temperature and pressure of the isostatic press are maintained for approximately 0.75 hours. The temperature is then reduced to room temperature after which the pressure is released. After pressure has been released and the hot isostatic press has been cooled to room temperature, the hot isostatic press is opened and the container is removed. The container is then opened to reveal a slab of biocompatible material stock in which the voids are reduced.

EXAMPLE 5

A biocompatible component in the form of a stem of a hip joint prosthesis described above is initially formed from carbon fibers which are encapsulated by a polysulfone. The biocompatible component is then ultrasonic cleaned in water to remove surface containments. The biocompatible component is then subjected to a grit blasting operation. In this regard, the portions of the biocompatible component which are not to receive the porous coating are initially covered with polyvinyl chloride tape. The biocompatible component is then placed in front of grit blaster operating at 40 psi with a ½ inch nozzle using a 16 grit silicon carbide particles. By grit blasting the biocompatible component, a roughen surface is formed in the region which is exposed to the particles. The polyvinyl chloride tape is then removed from the biocompatible component.

It will be appreciated that other means may be used for obtaining a roughened surface on the biocompatible component. For example, a ¹⁄₁₆' drill bit may be used to form the roughened surface. In this regard, the drill bit may be randomly disposed against the portion of the biocompatible component where the roughened surface is to be formed thereby generating a plurality of holes. This process is continued until the desired surface roughness is obtained. A dove-tail cutter may also be used to form the roughened surface. In this regard, a dove-tail cutter having a cutting surface of a maximum of ¹⁄₃₂' in diameter may be disposed against the surface of the biocompatible component which is to be roughened and then the axis of rotation of the cutter is moved in a circular fashion. The dove-tail cutter is then removed from the biocompatible component and then disposed against another portion of the surface of the biocompatible component. This process is repeated until the desired surface roughness is obtained.

The biocompatible component is then cleaned in a second ultrasonic cleaning operation. The portions of the biocompatible component which are not to receive the porous coating are then covered with heat tape which is resistant to the high temperature which are to be generated during the plasma spray operation. Care is taken so that the portions of the biocompatible component which are covered by the porous coating are not physically contacted after the second ultrasonic cleaning operation until the porous coating is applied. In this regard, the storage rack which is used to transport the biocompatible component to the plasma spray chamber supports the biocompatible component only at those areas which are not to be coated with porous coating.

The biocompatible component is then placed in a plasma spray chamber in such a manner that portions of the biocompatible component which receives the porous coating is not touched. The spray chamber is initially evacuated to approximately 10 millitorr and then backfilled with argon gas to a pressure slightly above atmospheric. The plasma spray is then applied to the biocompatible component for a period of approximately 20 seconds. After the plasma spray has been applied for this period of time, the biocompatible component is placed in front of the exhaust fan of the spray chamber for approximately 1 minute.

This process of applying the plasma spray and then cooling the biocompatible component is repeated approximately 8 times. The biocompatible component is then removed from the spray chamber and then sandpaper is used to remove loose material from the biocompatible component. The biocompatible component is washed in a water jet operating at 900 psi to remove additional residue.

The biocompatible component is then placed in a stainless steel container of the type described above which is then filled with zirconium oxide beads. The container is then evacuated and sealed. The container, together with the biocompatible component, is then placed in a hot isostatic press and then the hot isostatic press is closed. The temperature of the hot isostatic press is then increased from room temperature to approximately 430° F. and while the pressure is increased to 7500 psi. The temperature and pressure of the hot isostatic press are maintained for approximately 45 minutes. The temperature of the hot isostatic press is then allowed to cool to approximately 100° F. over a one hour time period and then the pressure of the hot isostatic press is decreased to atmospheric over a thirty-minute time period. The hot isostatic press is then cooled to room temperature after which the hot isostatic press and the container is removed. The container is then opened to reveal a biocompatible component with the porous coated surface relatively securely attached.

Figure 11:
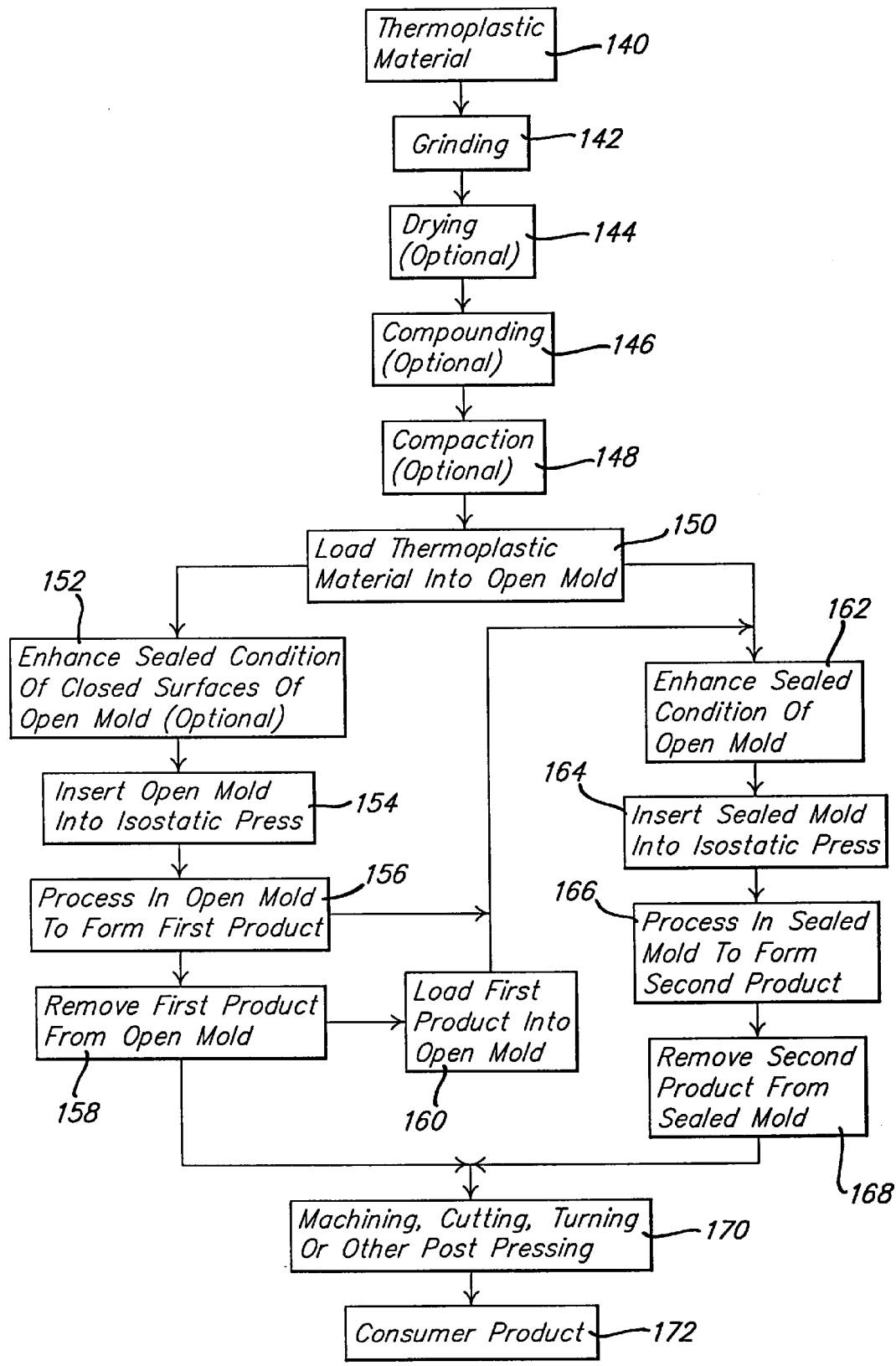
FIG. 11 is a flow diagram illustrating the steps for forming an article from recyclable thermoplastic waste material according to a preferred embodiment of the present invention.

According to another preferred embodiment of the present invention, there is provided a method and apparatus for forming an article from a thermoplastic material, which may preferably be a recyclable thermoplastic waste material, as illustrated in FIGS. 11–18. With reference now to FIG. 11, there is shown a flow diagram illustrating the steps of the preferred embodiment of the method of the present invention. The method of the preferred embodiment of the present invention will now be described with reference to FIG. 11 which comprises the steps 140 through 172.

At step 140, a thermoplastic material is provided. Preferably, the thermoplastic material is a recyclable thermoplastic waste material, although it will be appreciated that other types of thermoplastic materials may be used. Typically, the thermoplastic material will be post-consumer household thermoplastic waste, which may be collected by curbside residential pickup or by community collection bins. The thermoplastic material may be also be in the form of industrial thermoplastic waste. The thermoplastic material may also typically include dirt, metals or other impurities.

Some examples of the varieties of thermoplastic materials suitable for use with the method of the present invention include polyethlyeneterephthalate (PET), high and low density polyethylene, rigid and non-rigid polyvinyl chloride (PVC), other vinyl compounds, polyester, polystyrene and polyamide. Some typical sources of these types of thermoplastic materials include plastic toys, milk jugs, pesticide bottles, liquid laundry and dishwasher detergent bottles, polyester films and other film products, nylons, rigid plastic plates and cups and vinyl household products such as seating surfaces and notebook binders. Typically, such a mixture of thermoplastics is difficult to recycle because of degassing problems of some of the thermoplastic material varieties, the inability to mix the different varieties of thermoplastic material and the difference in melt temperatures among thermoplastic components, which usually varies between 300° F. and 400° F., however, higher temperatures may be utilized with modifications to the processing equipment. The method of the present invention, however, is able to process most of the above types of thermoplastic materials without suffering from these disadvantages.

The reclaimed thermoplastic material is first subjected to a grinding treatment as indicated by the step 142. During the grinding treatment, the thermoplastic material is reduced to small sized particles through methods well-known to those skilled in the art. For example, the thermoplastic material may be fed directly into a standard scrap grinder which includes a series of intermeshing knives. This process is operable for reducing the thermoplastic material to pieces having a size of approximately one-quarter to one-half inch. It will be appreciated, however, that any size of particles from this size down to a powderized form resulting from the grinding step is suitable for this method. It is preferred that the thermoplastic material be ground to smaller sized particles, as long as this is practical given cost considerations.

Following the grinding step 142, the ground thermoplastic material may optionally be dried. Drying of the ground thermoplastic material is preferred if the selection of subsequent process steps will not accomplish a drying of the material. It is preferred that the thermoplastic material be dried at this point when producing a substantially completely densified end product through the steps 162–168 set forth below, because the mold used in those steps does not afford the same drying capability as does the mold used in steps 152–158. Drying at this point is also preferred where there will be insufficient heating chosen in subsequent steps to cause an evaporation of water from the thermoplastic material. Preferred methods for accomplishing the drying step 144 include subjecting the thermoplastic material to heat, subjecting the thermoplastic material to a vacuum, and blowing air through the material.

In the next step of the method of the present invention, designated as step 146, the thermoplastic material is optionally compounded. This step contemplates the introduction of any additives to the thermoplastic material that might affect the final product characteristics or the processing characteristics at any subsequent processing step. One example of a suitable additive is carbon black, which coats the thermoplastic material particles, and allows a surface area for radio frequency excitation during heating of the material within the isostatic press, if radio frequency heating is selected. Other suitable additives include dyes and pigments for altering the color or consistency of the end product, coatings for enhancing the appearance and/or external surface characteristics of the product and ultraviolet stabilizers that impart in the end product a resistance to fading and breakdown due to exposure to sunlight.

The thermoplastic material may also optionally be subjected to a compaction treatment at step 148. This optional step contemplates forming the ground thermoplastic material into a compacted, but not densified material. Compacting may facilitate handling of the thermoplastic material and may also result in reduced shrinking of the material during the molding process, each resulting in improved efficiency of the overall process. Preferably, the compaction step is accomplished by a mechanical compaction process. A preferred example is placing the thermoplastic material into a ram-type extruder, although it will be appreciated that other suitable methods, including manual methods, may be used. The compaction step 146 may often produce bars or rods of round, rectangular or other cross-sectional shape in sizes ranging from approximately one-inch to 12-inch width. One typical size is a bar having a one-inch by three-inch rectangular cross-section. The compaction step 146, however, should produce a compacted material of a size suitable for being insertable into the mold and isostatic press equipment discussed below.

According to the next step of the present invention, designated as step 150, the thermoplastic material, in either ground or compacted form, is placed into a mold. A first preferred type of mold is shown at 200 in FIGS. 12 and 13, which illustrate two cross-sectional views, 90° removed from each other, of an open-type, or open, mold. The mold 200 is a preferred type of mold for use with the steps 152–158 of the present invention, where gas pressure within the isostatic press is allowed to directly contact the thermoplastic material through the open end of the mold.

Steps 152–158 of the present invention are used when it is desirable to produce a partially densified product, designated as a first product in FIG. 11. This product is typically 70% to 85% densified, as compared to the substantially completely densified product resulting from the process of steps 162–168 which will be described in further detail below. The partially densified first product derived from steps 152–158 may itself be a suitable consumer product for many purposes. The partially densified first product resulting from steps 152–158 may also be subsequently processed according to steps 162–168, either using the mold 200, or by removing the first product from the mold 200, and then continuing with the steps 162–168 as will be described below.

The mold 200 is shown to include an outer surface 202 which is of generally rectangular shape. It will be appreciated, however, that the mold 200 may have any suitable exterior shape, as long as such shape allows the mold 200 to be enclosed within the isostatic press as discussed below. The mold 200 may be constructed of a rigid material suitable for containing a thermoplastic material during an isostatic press treatment. The mold 200 should preferably also be constructed of a material suitable for resisting the infiltration of a liquid pressurized fluid, such as oil, into the mold material itself during the isostatic press treatment. Suitable selections for rigid varieties of the mold 200 include aluminum, brass, steel, copper and cast epoxy, or any other suitable material that would not melt at processing temperatures. Alternatively, the mold 200 may be constructed of an elastomeric material, such as silicone rubber.

The mold 200 is also shown to define a mold cavity 204 which may preferably be shaped by varying each of the three dimensions of the mold cavity 204, in order to produce an end product whose shape is preselected in each dimension. This configuration allows the method of the present invention to produce articles whose cross-section may vary over their length, thus providing an advantage not realized in extruded products. For example, in FIGS. 12 and 13, the mold cavity 204 is shown to be shaped for the formation of a picket fence post. It will be appreciated, however, that the mold cavity 204 may be shaped to cause the formation of any desired shape of product.

Figure 12:
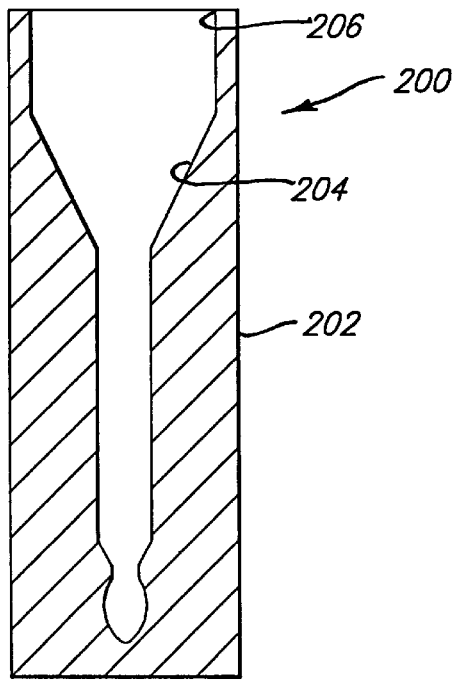
FIG. 12 is a cross-sectional view of a mold according to a preferred embodiment of the present invention.
Figure 13:
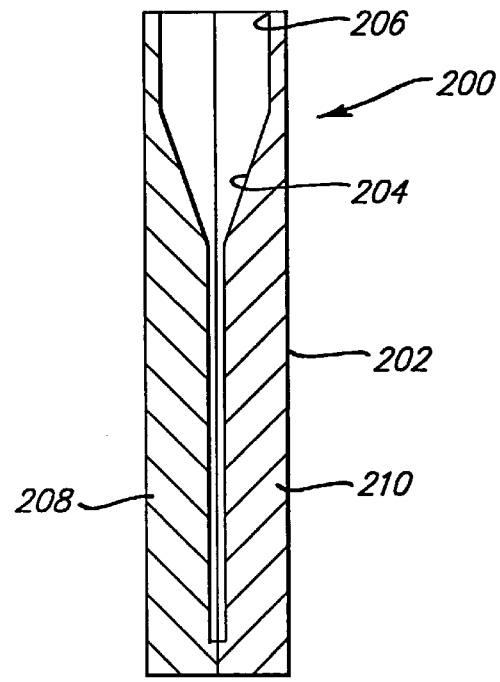
FIG. 13 is a cross-sectional view of a mold from a view 90° removed from that of FIG. 12.

The mold 200 is further shown to include an aperture 206 through which the thermoplastic material may be introduced. The aperture 206 is preferably configured and sized to allow a substantially open mold at one end, as shown in FIGS. 12 and 13. This arrangement is desirable because when the mold 200 is oriented within the isostatic press with the aperture 206 adjacent to the top of the press, it allows gas pressure within the press to act directly upon the thermoplastic material contained within the mold 200. Alternatively, the aperture 206 may be of different suitable configurations and sizes as may be desirable to accomplish the molding process. The presence of the aperture 206 also may allow compacted thermoplastic material to protrude from above the top surface of the mold 200 to a limited extent upon insertion into the mold 200. In this arrangement, the heat applied during the isostatic press treatment will allow the compacted thermoplastic material to melt and be forced downward into the mold. Also, during processing, the thermoplastic material convectively mixes inside the mold.

The mold 200 may be of unitary construction, or may more typically be constructed of two or more complimentary mold portions which are subsequently assembled to form a complete mold. As shown in FIG. 13, the mold 200 is shown to comprise a first mold portion 208 and a second mold portion 210. The first mold portion 208 and second mold portion 210 may preferably be complimentary halves of a complete mold. Other suitable configurations for the mold 200 include four discrete mold portions, each mold portion representing a one-fourth section of the assembled mold, which may be brought together in a complimentary fashion to form the complete mold. The complimentary mold portions may include one or more sealing members (not shown), such as O-rings or gaskets, which may be integrated directly into the construction of the mold portions, or may be auxiliary attachment devices that are used when the mold is assembled.

At the same time the thermoplastic material is introduced into the mold, which is the mold 200 for steps 152–158, other materials may optionally be introduced into the mold 200 with the thermoplastic material. An example of one such class of materials is coating materials for enhancing the external appearance and/or surface characteristics of the final product, such as porous coating materials for increasing surface area of anodes and cathodes for electrochemical processing. One or more of these materials may be applied either directly to the surface of the mold cavity 204 or may be introduced in a controlled fashion with the thermoplastic material, such as by simultaneous controlled feeding, or by coating the surface of a compacted thermoplastic material. Another type of optional material is mold release agents for facilitating removal of the product following molding. Various types of reinforcement devices (not shown), including rods, grids, scaffolding or other reinforcing materials made from metals, polysulfone or any other materials suitable for enhancing the structural stability of the final product may also be introduced into the mold at this time. Such reinforcement materials may be in the form of a single reinforcement substantially surrounded by thermoplastic material, or may be multiple reinforcements integrated into the thermoplastic material. As such, they are preferably inserted into the mold along with the thermoplastic material in a controlled manner, or after a portion of the thermoplastic material has been inserted into the mold cavity 204. It will be appreciated that other suitable reinforcement arrangements may also be used.

In the next step of the method of the present invention, where the mold 200 is formed from a plurality of complementary mold portions, step 152 may be optionally employed to enhance a sealed condition of the closed surfaces of the mold 200. The closed surfaces are defined as those surfaces located apart from the aperture 206, which may be submerged in a liquid pressure/heat transfer medium, should one be used as a pressurizing medium. The purpose for this step is to inhibit the undesirable introduction of liquid pressure/heat transfer medium into the interior of the mold cavity 204 during the isostatic press treatment. In step 152, a substantially sealed condition of the closed surfaces of the open mold may optionally be enhanced by the application of one or more sealing devices (not shown) to the outer surface 202 of the mold 200 along seams created by the junction of adjoining mold portions, such as the first mold portion 208 and the second mold portion 210. Examples of such sealing devices include sealing tapes, such as silicone tape, and adhesives. Alternatively, other types of suitable sealing devices may be used. For example, the mold 200 may optionally be substantially surrounded on all surfaces except for the aperture 206 with a high temperature silicone or elastomeric sleeve or bag to further enhance the sealed condition of the closed surfaces of the mold 200.

In step 154 of the method of the present invention, the mold 200 is inserted into an isostatic press. The isostatic press is preferably a hot isostatic press and may preferably be of the type represented by the hot isostatic press 46 in FIG. 4. Referring now to FIG. 16, there is shown a hot isostatic press 220. The hot isostatic press 220 shown in FIG. 16 is substantially similar to the hot isostatic press 46 shown in FIG. 4, except that the hot isostatic press 220 utilizes heating coils as a substitute for the heating elements 60 described above. Thus, for purposes of explaining the present method, references will be made to the hot isostatic press 220 shown in FIG. 16. It will be recognized, however, that either embodiment of hot isostatic press may be used.

Referring again to FIG. 16, the hot isostatic press 220 is shown to include a pressure chamber 222 which is defined in part by an annular wall 224, the thickness of which may preferably be between about three inches and about six inches. In one arrangement, the pressure chamber 222 may preferably be about eighteen inches in diameter and about fifty-three inches in length. It will be appreciated, however, that the size of the hot isostatic press 220 may vary depending upon the processing needs, including the desired final product size. For example, the hot isostatic press system may utilize existing standard hydraulic equipment, and may also utilize standard gas cylinders and boosters. For this reason, any suitable size hot isostatic press may be used which accomplishes the desired result.

The hot isostatic press 220 further includes a lower closure 226 and upper closure 228 which are threadedly attached to the annular wall 224 by matching buttress threads 230 and 232. It is to be understood, however, that a pin locking mechanism or tie rod assembly (not shown) may also be employed for securing the lower closure 226 and upper closure 228 to the annular wall 224. The lower closure 226 and upper closure 228 are operable to maintain a heated and pressurized condition within the pressure chamber 222 during the hot isostatic pressure treatment described below.

The hot isostatic press 220 further includes a plurality of heating coils 234 that are operable to generate thermal energy within the pressure chamber 222. This is accomplished by the transfer of a heating fluid through the heating coils 234 during the hot isostatic pressure treatment operation. Alternatively, the hot isostatic press 220 may include another heating means, such as the resistance heating elements 60 described in connection with FIG. 4, or radio frequency heating plates or induction heating. The hot isostatic press 220 may also include a cooling jacket of the type shown in FIG. 4 as 62, which comprises a plurality of coils encircling the annular wall. Alternatively, the cooling function may be accomplished by any other suitable cooling means which may be disposed at a different location within the hot isostatic press 220, such as within the pressure chamber 222 or between the pressure chamber 222 and the annular wall 224. The hot isostatic press 220 may also include a heat shield (not shown) of the type described at 64 in connection with FIG. 4, located between the annular wall and the heating elements. The heat shield is operable to limit heat losses from within the pressure chamber 222 and to assist in controlling the temperature within the pressure chamber 222.

The hot isostatic press 220 also includes a pressure system (not shown) of a type well-known to those skilled in the art that is operable to pressurize the pressure chamber 222. The pressure system also communicates with the pressure chamber 222 by means of a pressure input/output line 236 that is connected to an inert gas source and compressor of a type well known to those skilled in the art. In a preferred embodiment, the inert gas is argon, although nitrogen, helium and neon gases may also be used.

The hot isostatic press 220 further includes a transfer system for circulating a heating fluid though the heating coils 234 during operation. This system includes heat transfer fluid inlets 238 and 240 and heat transfer fluid outlets 242 and 244. The hot isostatic press 220 also includes a drain 246 for draining a liquid pressure/heat transfer medium from within the pressure chamber 222. A static line 248 is also provided for monitoring pressure inside the pressure chamber 222. The hot isostatic press 220 also is shown to include a drainage line 250 and valve 252 for regulating the upper level of liquid pressure/heat transfer medium within the pressure chamber 222, when a liquid pressure/heat transfer medium is used. It will be appreciated that the hot isostatic press 220 is suitable for utilizing water, oils or inert gases, or a combination of these as one or more pressure fluids, used either in combination or sequentially. The hot isostatic press 220 further includes a power distribution system (not shown) of a type well-known to those skilled in the art. The power distribution system is used for controlling the heat and pressure within the pressure chamber 222.

The hot isostatic press 220 is operable to change the temperature within the pressure chamber 222 from an initial room temperature of from about 60° F. to about 70° F. to an operating temperature from about 350° F. to about 600° F. A preferred operating temperature is from about 385° F. to about 400° F. In addition, the hot isostatic press 220 is also operable to change the pressure within the pressure chamber 222 from approximately atmospheric pressure to an operating pressure of from about 500 pounds per square inch to about 60,000 pounds per square inch. Preferred operating pressures are generally from about 1,000 pounds per square inch to about 3,000 pounds per square inch. One reason for this preferred range is because isostatic presses that are considered standard hydraulic equipment, and are thus a preferred type of equipment, are typically operable to change the pressure within the pressure chamber 222 from approximately atmospheric pressure to an operating pressure of up to about 3,000 pounds per square inch. The hot isostatic press 220 may be of a type available from those manufacturers described previously in connection with FIG. 4, e.g., manufacturers of hollow forged components, such as Hydro-Pac of Bearview, Pa.

According to the preferred method of the present invention, at step 154, the mold 200 is inserted into the hot isostatic press 220. Preferably the mold 200 is disposed within the pressure chamber 222 in a standing orientation, such that the aperture 206 is located at the top of the mold 200. It will be appreciated, however, that other suitable orientations may be used. The hot isostatic press 220 is then closed by threading the upper closure 228 onto the annular wall 224 by the buttress threads 232. A vacuum of at least approximately 27 in. Hg is then optionally applied to the pressure chamber 222 by means of connecting the pressure input/output line 236 to a suitable vacuum source (not shown).

Figure 17:
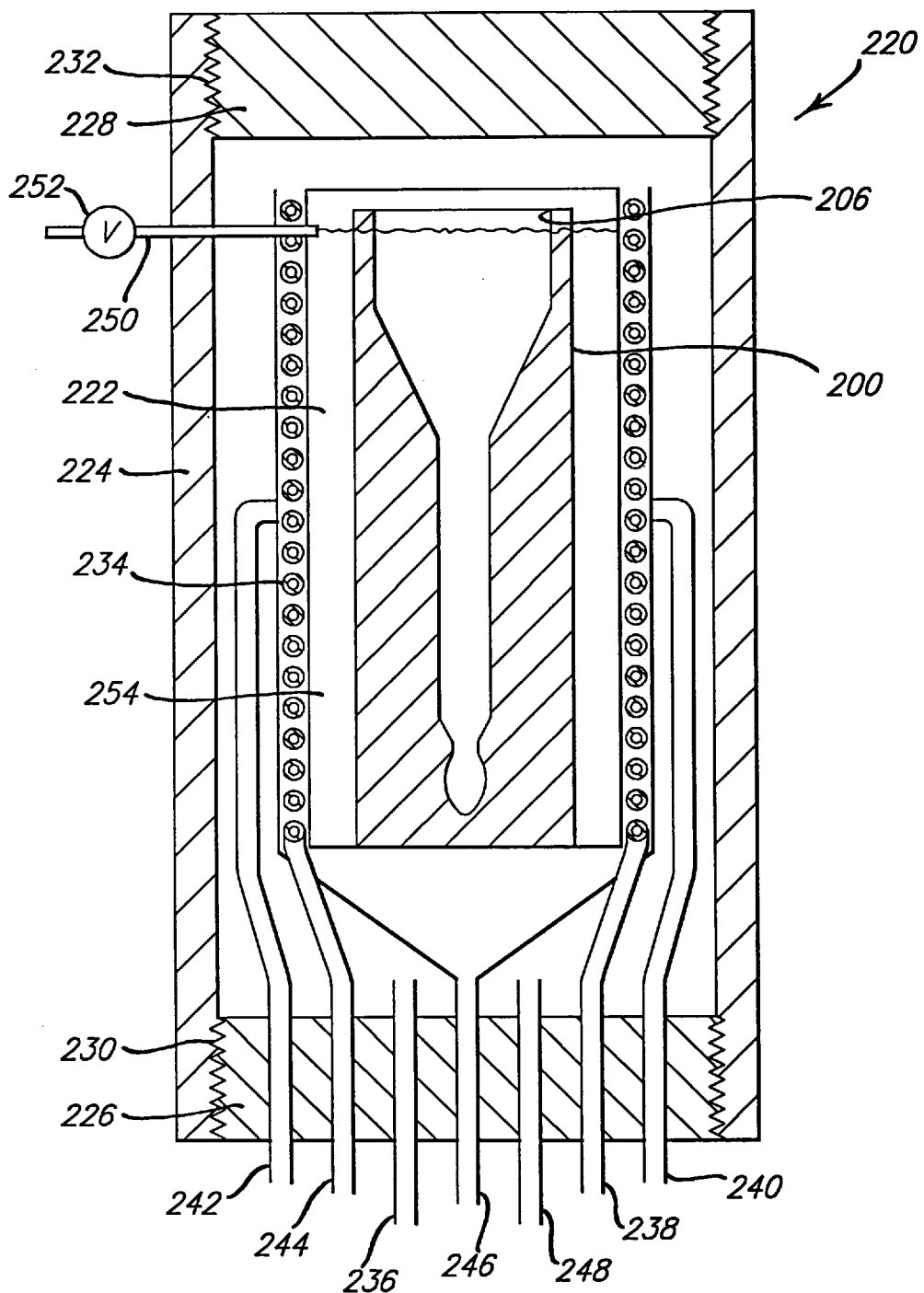
FIG. 17 is a cross-sectional view illustrating an isostatic press containing the mold illustrated in FIGS. 12 and 13.

In the next step of the method of the present invention, step 156, the thermoplastic material is processed in the mold 200 to form a first product. Where a liquid pressure/heat transfer medium is used, the liquid pressure/heat transfer medium is introduced into the pressure chamber 222 at this time. The liquid pressure/heat transfer medium is delivered into the pressure chamber 222 by any suitable means, such as through drain 246, or through any other suitable port, preferably until the liquid pressure/heat transfer medium level reaches a level such that the thermal expansion of the medium will not cause the level to rise above the upper edge of the mold 200. This level may preferably be approximately one inch below the upper edge of the mold 200. FIG. 17 is a cross-sectional view illustrating the mold 200 disposed within the pressure chamber 222, with a liquid pressure/heat transfer medium 254 disposed within the pressure chamber 222 to approximately one inch from the top surface of the mold 200, as defined by the aperture 206.

Once the liquid pressure/heat transfer medium is introduced, if one is used, the pressure chamber 222 may optionally be evacuated by applying a vacuum of at least approximately 27 in. Hg to gas inlet 236, or another suitable port or port and valve arrangement. At this time, heat is applied to accomplish the operating temperatures discussed above by circulating heated fluid through the heating coils 234. Also, pressure is applied to accomplish the operating pressures discussed above by introducing an inert gas into the pressure chamber 222, such as through gas inlet 236. Alternatively, an inert gas may be used as the only pressure medium, and no liquid pressure/heat transfer medium is introduced into the pressure chamber 222. Generally, the use of an inert gas as the sole pressure fluid results in longer processing time as compared to the use of a liquid pressure/heat transfer medium. Typically, the thermoplastic material is processed in the mold 200 for approximately two hours for a four-inch diameter bar, although shorter or longer times may be used, depending upon the operating temperature, operating pressure, selection of pressure fluid, thermoplastic material particle size, type of thermoplastic material being processed and type of equipment being used. The time selected should be sufficient for the thermoplastic material to become between approximately 70% and approximately 85% densified. The processing time may also be increased or decreased according to the desired final density of the product. Typically, higher operating pressures of the hot isostatic press 220 require less increase in temperature to achieve the same final densification. After the hot isostatic press treatment is completed the hot isostatic press 220 is allowed to cool or may optionally be cooled through the use of auxiliary cooling coils as described previously, or by circulating a cooling medium through the heating coils 234.

Once processing of the thermoplastic material is complete and the first product is formed, the mold 200 and first product are removed from within the pressure chamber 222. This may be accomplished by dethreading the upper closure 228 from the annular wall 224 through the buttress threads 232, to open the hot isostatic press 220. As shown in FIG. 11, further processing of the first product to achieve a substantially fully densified product or other product may take place by subjecting the first product to the process of the steps 162–168 while remaining within the mold 200. When this is desired, the mold 200 containing the first product should be of the type which may be subsequently substantially closed and processed as described below in connection with the steps 162–168.

When the first product is not subjected to the process of the steps 162–168 while remaining within the mold 200, the first product is removed from the mold 200, according to step 158. This step may first include the removal of a silicone or elastomeric sleeve or bag previously disposed upon the closed surfaces of the mold 200. This step may also include removing any sealing devices such as tapes, which were previously applied to the mold 200 for enhancing a sealed condition of its closed surfaces. For open molds 200 which are constructed of two or more mold portions, the mold portions are separated from each other at this time. The first product is then removed from the mold 200. The first product may then, according to step 160, be subjected to the process of the steps 162–168 by inserting the first product into an open mold which is subsequently closeable for use with the process of those steps. Optionally, the first product may be inserted into or surrounded by an elastomeric bag, a foil bag, foilized shrink tubing, polytetrafluoroethylene shrink tubing or polyvinylchloride shrink tubing, in one piece or in the form of a multi-piece assembly, prior to being subjected to the process of the steps 162–168.

Figure 14:
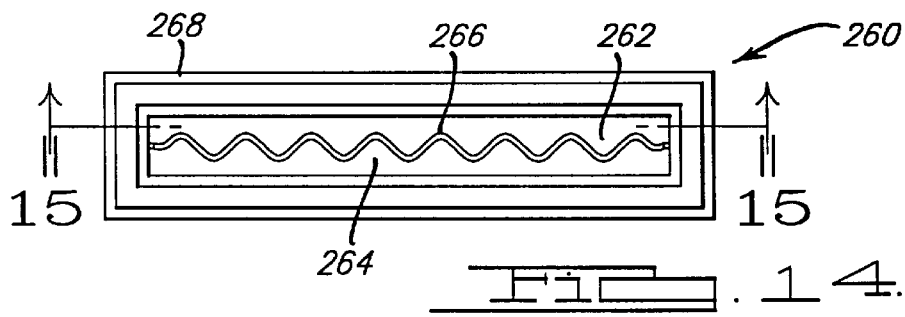
FIG. 14 is a top view of a mold, absent a closure, used in accordance with the method of the present invention.
Figure 15:
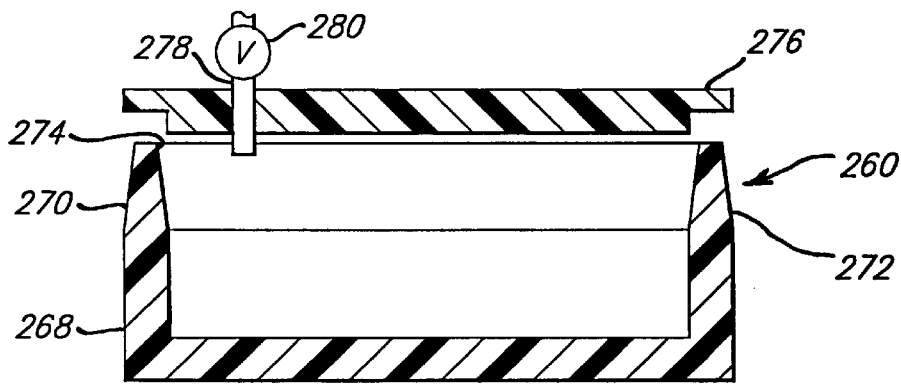
FIG. 15 is a side view of the mold illustrated in FIG. 14 with associated closure.

Referring again to FIG. 11, at step 150, the thermoplastic material may, from the start, be alternatively introduced into another preferred type of mold suitable for use in the process of steps 162 through 168. Referring now to FIGS. 14 and 15, there is shown a top view and a side cross-sectional view of a second type of mold to be used with steps 162 through 168. This mold, shown at 260, is shown to be a closed mold which, in this form, is a mold for producing a noise abatement tile as the desired final product. The mold 260 is shown to include a first die 262 and second die 264 which are preferably complimentarily shaped so as to form an molding space 266 therebetween when the first die 262 and the second die 264 are brought together in a complementary relation. The first die 262 and the second die 264 may be constructed of a suitable metal such as those metals described above as being suitable for the mold 200, or may alternatively be constructed of an elastomeric material. The molding space 266 is suitable for the introduction of thermoplastic material, either in ground form, or in compacted form where the dimensions of the molding space 266 will allow. The mold 260 may also preferably be substantially surrounded by a silicone or elastomeric sleeve 268 on its sides and bottom surface. The sleeve 268 acts as a fluid to transfer pressure over the entire surface of the article being molded. It will be appreciated that the sleeve 268 may be constructed of other suitable materials.

As can be seen in FIG. 15, one preferred arrangement for the sleeve 268 is to include tapered regions 270 and 272 extending above the upper surface of the first die 262 and the second die 264. Preferably, the tapered regions 270 and 272 extend approximately six inches above the upper surface of the first die 262 and the second die 264. Alternatively, other dimensions for the tapered regions 270 and 272 may be used. The tapered regions 270 and 272 may also be corrugated or may in some other arrangement be suitable for promoting a collapsing of these sections of the sleeve 268 during the subsequent isostatic press treatment. A preferred arrangement for this region of the sleeve 268 is for the tapered regions 270 and 272 to be previously deformed in the shape of a bellows, to promote a controlled collapse of this section upon the application of heat and pressure. As such, the tapered regions 270 and 272, disposed about the perimeter of the mold 260, form an aperture 274 above the upper surface of the mold 260.

As shown in FIG. 15, the mold 260 also includes a closure 276 for enhancing a substantially sealed condition of the mold 260 during the subsequent isostatic press treatment. The mold 260 also is shown to include a vacuum line 278 that is operable for being connected to an external device for producing a vacuum of at least approximately 27 in. Hg within the mold 260. A valve 280 is also provided on the vacuum line 278 for closing the vacuum line 278 for maintaining a vacuum within the mold 260 prior to the isostatic press treatment.

In this version of step 150 of the present invention, thermoplastic material is introduced into the molding space 266. Preferably the thermoplastic material introduced into the mold 260 is ground thermoplastic material, although compacted thermoplastic material may also be introduced. As before, additives, mold release agents, reinforcement materials, or any other additives may also be introduced into the molding space 266 at this time, in any of the arrangements previously mentioned. Additional ground or compacted thermoplastic material may also optionally be introduced above the upper surfaces of the first die 262 and the second die 264 within the enclosure created by the tapered regions 270 and 272. Preferably, any additional thermoplastic material inserted above the surfaces of the first die 262 and the second die 264 will allow sufficient space within the enclosure created by the tapered regions 270 and 272 for the proper insertion of any portion of the closure 276 to be insertable into the aperture 274. As such, where the tapered regions 270 and 272 provide six inches above the surface of the first die 262 and the second die 264, a maximum of four inches of additional thermoplastic material will be inserted above the surfaces of the first die 262 and the second die 264, so that the typical two inches taken by the closure insertion may be subsequently accomplished. In other arrangements, different dimensions must be maintained in order to close the mold properly.

At step 162 of the method of the present invention, the mold 260 is enhanced in a substantially sealed condition. This is accomplished by placing the closure 276 in contact with the tapered regions 270 and 272 so as to substantially cover the aperture 274 formed thereby. One or more sealing devices may then preferably be applied to the closure 276 for enhancing a substantially sealed condition of the mold 260. Suitable selections for sealing devices include one or more mechanical clamping devices, such as one or more hose clamps. Alternatively, an adhesive may be used upon one or more surfaces of the closure 276 and/or the tapered regions 270 and 272 to enhance a sealed condition, such as a hot melt glue. Other suitable sealing devices may also be employed. An alternative arrangement for the mold 260 is to provide a substitute for the sleeve 268 in the form of a latex sleeve (not shown) which substantially surrounds the first die 262 and the second die 264 and may be enclosed along the top surface of the first die 262 and second die 264 by such means as tying or other suitable means. A vacuum of at least approximately 27 in. Hg is then preferably applied through a vacuum line such as 278 to substantially evacuate the sealed mold 260. The valve 280 is then closed to maintain this vacuum. Alternatively, the vacuum line 278 may be substantially sealed by an alternative mechanical means such as a hose clamp or other type of squeezing clamp. Preferably, valve 280 is in the form of a check valve. Where a first product contained within an mold 200 of the type previously described is subsequently subjected to the steps 162–168 to form a substantially completely densified second product, an option previously mentioned, the mold 200 is preferably also substantially sealed and evacuated at this time.

At step 164 of the method of the present invention, the mold 260, which is at this time a substantially sealed mold, or, alternatively, a substantially sealed version of the mold 200 from step 156, is inserted into an isostatic press. The isostatic press may preferably be of the type previously described in connection with FIG. 4 or the hot isostatic press 220 described in connection with FIG. 16. Alternatively, it will be appreciated that other types of isostatic presses may be used. For purposes of explaining the method of the present invention, reference will be made to the hot isostatic press 220 and the mold 260. The hot isostatic press 220, containing the mold 260, is then closed by threading the upper closure 228 onto the annular wall 224 by the buttress threads 232, as before. A vacuum is then optionally applied to the pressure chamber 222 by means of connecting the pressure input/output line 236 to a suitable vacuum source (not shown), as before.

According to step 166 of the method of the present invention, the thermoplastic material is processed in the mold 260 to form a second product. The second product is distinguishable from the first product in that it is substantially completely densified, as compared to the 70% to 85% density of the first product formed by the steps 152–158.

Figure 18:
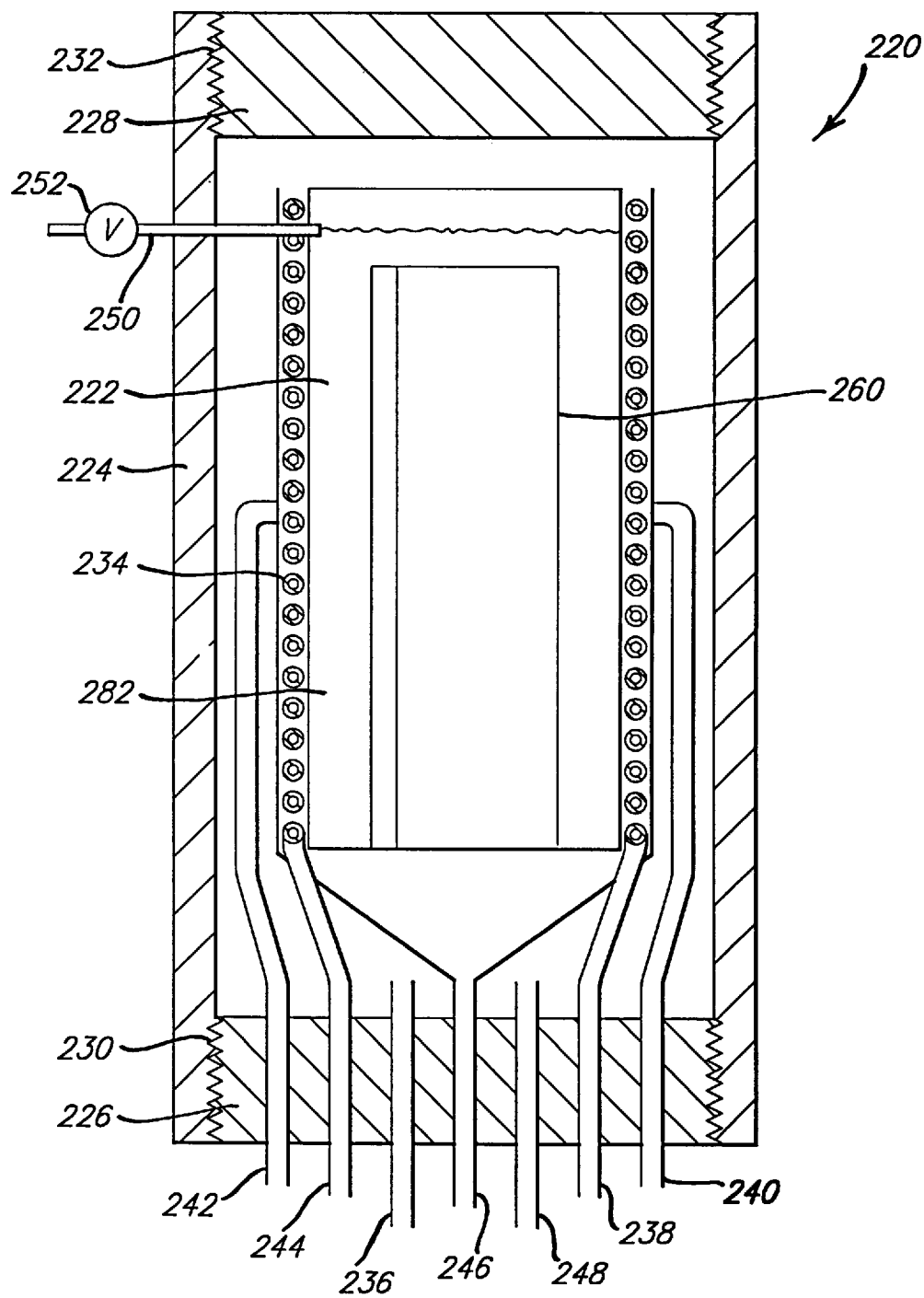
FIG. 18 is a cross-sectional view illustrating an isostatic press containing the mold of FIGS. 14 and 15.

As shown in FIG. 18, a liquid pressure/heat transfer medium is then introduced into the pressure chamber 222 so as to substantially submerge the mold 260 disposed therewithin. Preferably, the mold 260 remains standing on the bottom of the pressure chamber 222, although the sealed mold may alternatively float or experience some buoyancy during the isostatic press treatment.

The hot isostatic press 220 is then operated in a similar manner as before to melt the thermoplastic material and densify it, this time to a substantially fully densified material. During this process, the temperature and pressure ranges and time periods are substantially as previously described. The gas pressure applied into the pressure chamber 222 preferably operates to compress the sleeve 268, especially the tapered regions 270 and 272 disposed above the first die 262 and second die 264. In an alternative embodiment, a liquid pressure/heat transfer medium is not utilized, and the gas pressure is used alone to compress the thermoplastic material, as before.

In step 168 of the present invention the second product is removed from the mold 260. At this time, air from the surrounding atmosphere may be allowed to enter the pressure chamber through pressure input/output line 236. The hot isostatic press 220 is then opened by dethreading the buttress threads 232 between the upper closure 228 and the annular wall 224, as before. The mold 260 is then removed from within the pressure chamber 222. At this time, the valve 280 may be opened to allow air from the surrounding atmosphere to enter the mold 260 through the vacuum line 278. The optional latex sleeve, if one has been used, may then be removed from the exterior of the mold 260. In the embodiment where a sleeve 268 and associated closure 276 has been used, it is removed at this time. The opening of the closure 276 may sometimes require mechanical means for breaking the seal previously made. This can be accomplished by working around the perimeter of the closure 276 with a screwdriver or other mechanical device. In some applications, the sleeve 268 may be of the type having a memory shape, which tends to return substantially to its original shape upon the opening of the valve 280.

Both the first product produced from steps 152–158 and the second product produced from steps 162–168 of the present invention may be useful articles. Optionally, the first product and/or the second product may be subjected to one or more types of post-pressing mechanical treatment, such as machining, cutting, turning or other mechanical treatment, as shown at step 170 in FIG. 11. This process yields a consumer product, represented at step 172. Some examples of useful articles made from the process of the present invention include structural and non-structural components including planters, sound barriers, fences, stakes, boards, erosion control materials, road barriers, piers, boat fenders, boardwalks, docks, wear plates, road delineators, desert waterway control components, gardening components, retaining walls, compost bins, recreational sandboxes, stadium seats and shipping pallets.

Figure 19:
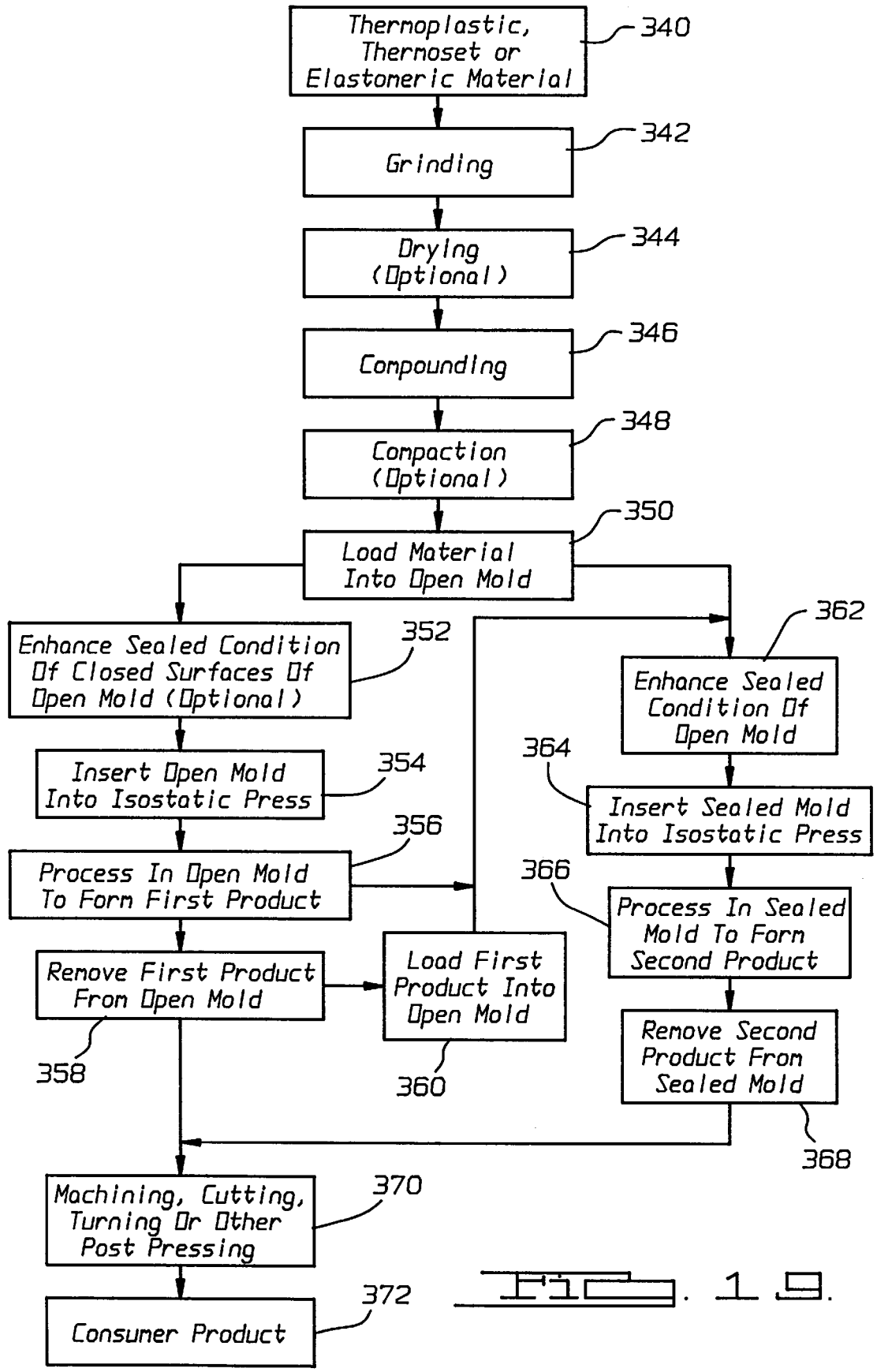
FIG. 19 is a flow diagram illustrating the steps for forming an article from recyclable thermoplastic, thermoset and elastomeric waste material according to a preferred embodiment of the present invention.

According to another preferred embodiment of the present invention, there is provided a method and apparatus for forming an article from a recyclable waste material. At least several of the steps of this embodiment of the present invention may be performed in either a batch process or in a continuous process. The waste material may preferably be a thermoplastic, thermoset or elastomeric material, or mixtures of these materials, and may also be a waste material wherein at least a portion of the waste material is selected from the group consisting of thermoplastics, thermosets, elastomers and mixtures thereof. This embodiment is set forth in FIGS. 19–22. With reference now to FIG. 19, there is shown a flow diagram illustrating the steps of a preferred embodiment of the method of the present invention. The method of this embodiment of the present invention will now be described with reference to FIG. 19, which comprises the steps 340 through 372. This method is similar to the method previously described with reference to FIG. 11, as described in steps 140 through 172. As such, it will be appreciated that many of the steps set forth below share similar descriptions to the steps 140 through 172; therefore, certain repetitive information in common with these steps will not be repeated below.

At step 340, a waste material is provided. Preferably, the waste material is a recyclable material, at least a portion of which is a material selected from the group consisting of thermoplastics, thermoset, elastomers and mixtures thereof. It will be appreciated that other types of waste materials may also be used. One specific example of waste material which may be used in the present method is used automobile tires. The waste material may typically include dirt, metals or other impurities.

The reclaimed waste material is first subjected to a grinding treatment as indicated by the step 342, in similar manner as before. This step contemplates grinding, granulating and pulverizing the waste material to a powder, as may be desired. Preferably, the waste material is reduced to particles having a size of from about 10 mesh to about 60 mesh. A preferred particle size is about 30 mesh.

Following the grinding step 342, the ground waste material may optionally be dried as described above. One alternative method for drying is subjecting the waste material to radio frequency heating. In the next step of the method of the present invention which is designated as step 346, the waste material is compounded with a binder material. This step contemplates mixing the ground waste material with a binder material in a preselected ratio of ground waste material to binder material thereby forming a waste-binder mixture. The binder may also be a reclaimed thermoplastic or ultra high molecular weight polyethylene, high density polyethylene, low density polyethylene, polyethlyene-terephthalate and other thermoplastics. Preferably the preselected ratio of ground waste material to binder material by weight is from about 80:20 to about 20:80. A preferred preselected ratio of ground waste material to binder material by weight is about 50:50. It will be appreciated that the desired ratio of waste material to binder material may depend upon the desired properties of the end product. Preferably, the binder material is in solid form, and is ground to substantially the same particle size as the ground waste material. It will be appreciated that other suitable binder materials may be used. It will also be appreciated that other suitable ratios of ground waste material to binder material may be used. The binder material is preferably operable for being converted at least partially to a state suitable for binding the ground waste material. This may be accomplished by heating the binding material thereby melting at least a portion of the binder material. Alternatively, the binder material may be of a form such that no heating is necessary for the binding to take effect. Optionally the binder material may be at least partially converted to a molten state by methods other than heating to bind the ground waste material. In the situation where the reclaimed material contains a substantial amount of thermoplastic material, a separate binder material addition may be omitted. A substantial amount of thermoplastic material is typically from about 30% to about 60% by weight.

As part of the compounding step, additives may be introduced to the waste material, or the waste-binder mixture, that might affect the final product characteristics or the processing characteristics at any subsequent processing step, as before. Examples of suitable additives include carbon black, and ultraviolet stabilizers, antioxidants, flame retardants and those previously mentioned in connection with step 146. It will also be appreciated that the compounding step may be accomplished in a rolling drum or in a large container with stirring capability, through which air may be blown to facilitate mixing.

The waste-binder mixture may also optionally be subjected to a compaction treatment at step 348. As before, this optional step contemplates forming the waste-binder mixture into a compacted but not densified material. Preferred methods for accomplishing the compacting step are those set forth previously with regard to step 148. Preferably, the addition of RF heat to the compacting step facilitates the production of a compacted material that may be handled by hand. This is advantageous, at least in part, due to the presence of carbon black in the reclaimed waste material, such as is present in used automobile tires. More preferably, radio frequency heating may be pulsed to optimize the heating of the binder material. It will be appreciated that this compacting process may be a batch or continuous process with cycle or residence times ranging from approximately 1 to approximately 20 minutes.

According to the next step of the present invention, designated as step 350, the waste-binder mixture is placed into a mold. A first preferred type of mold is shown at 400 in FIGS. 20 and 21, which illustrate two cross-sectional views 90° removed from each other, of an open-type or open mold. The mold 400 is a preferred type of mold for use with the steps 352–358 of the present invention where gas pressure within the isostatic press is allowed to directly contact the waste-binder mixture through the open end of the mold. In similar manner as steps 152–158 described above, steps 352–358 of the present invention are used when it is desirable to produce a partially densified product designated as a first product in FIG. 19. The product is typically 70% to 85% densified as with steps 152–158 above.

The mold 400 is shown to include an outer surface 402 which is of generally rectangular shape. It will be appreciated, however, that the mold 400 may have any suitable exterior shape as long as such shape allows the mold 400 to be enclosed within the isostatic press as discussed herein. The mold 400 may be constructed of a rigid material suitable for containing a thermoplastic material during an isostatic press treatment. The mold 400 should preferably also be constructed of a material suitable for resisting the infiltration of a pressurized fluid, such as oil or gas, into the mold material itself during the isostatic press treatment. Suitable selections for rigid varieties of the mold 400 include aluminum, brass, steel, copper and cast epoxy, or any other suitable material that would not melt at processing temperatures. Alternatively, the mold 400 may be constructed of an elastomeric material such as silicone rubber.

The mold 400 is also shown to define a mold cavity 404 which may preferably be shaped by varying each of the three dimensions of the mold cavity 404 in order to produce an end product whose shape is preselected in each dimension. This configuration allows the method of the present invention to produce articles whose cross-section may vary over their length, thereby providing an advantage not realized in extruded products. For example, in FIGS. 20 and 21, the mold cavity 404 is shown to be shaped for the formation of a board. It will be appreciated, however, that the mold cavity 404 may be shaped to cause the formation of any desired shape of product.

Figures 20, 21:
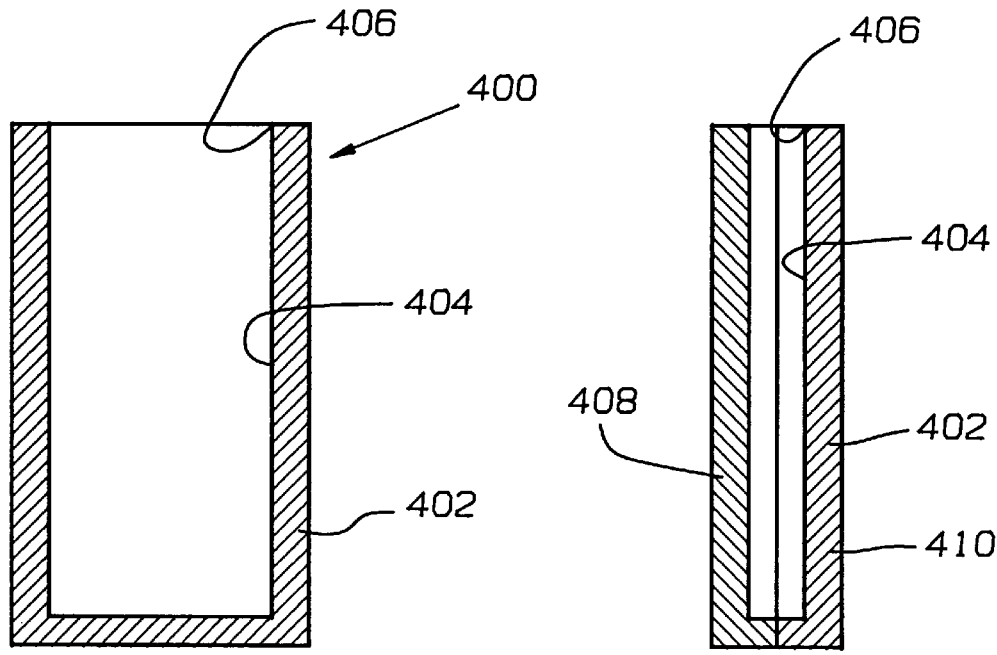
FIG. 20 is a cross-sectional view of a mold according to a preferred embodiment of the present invention.
FIG. 21 is a cross-sectional view of a mold from a view 90° removed from that of FIG. 20.

The mold 400 is further shown to include an aperture 406 through which the thermoplastic material may be introduced. The aperture 406 is preferably configured and sized to allow a substantially open mold at one end as shown in FIGS. 20 and 21. This arrangement is desirable because when the mold 400 is oriented within the isostatic press with the aperture 406 adjacent to the top of the press, the mold 400 allows gas pressure within the press to act directly upon the thermoplastic material contained within the mold 400. Alternatively, the aperture 406 may be of different suitable configurations and sizes as may be desirable to accomplish the molding process. The presence of the aperture 406 also may allow compacted thermoplastic material to protrude from above the top surface of the mold 400 to a limited extent upon insertion into the mold 400. In this arrangement, the heat applied during the isostatic press treatment will allow the compacted thermoplastic material to melt and be forced downward into the mold. Also during processing, the thermoplastic material may convectively mix inside the mold.

The mold 400 may be of unitary construction, or may more typically be constructed of two or more complimentary mold portions which are subsequently assembled to form a complete mold. As shown in FIG. 21, the mold 400 is shown to comprise a first mold portion 408 and a second mold portion 410. The first mold portion 408 and second mold portion 410 may preferably be complimentary halves of a complete mold. Other suitable configurations for the mold 400 include four discrete mold portions, each mold portion representing a one-fourth section of the assembled mold, which may be brought together in a complimentary fashion to form the complete mold. The complimentary mold portions may include one or more sealing members (not shown), such as o-rings or gaskets, which may be integrated directly into the construction of the mold portions or may be auxiliary attachment devices that are used when the mold is assembled.

Optionally, one or more components of the ground waste material may be separated for reclaiming or other purposes. One example of a material that is sometimes desirable for reclamation is the metal component of automobile tires. Metal from the ground waste material may be reclaimed magnetically by applying a magnetic field to the ground waste material. Alternatively, other separation techniques for separating metal or other components of the ground waste material may be used.

As before, at the same time the waste-binder mixture is introduced into the mold, which is the mold 400 for steps 352–358, other materials may optionally be introduced into the mold 400. These include coating materials, surface appearance enhancers, mold release agents and various types of reinforcement devices. Suitable selections for these additives are set forth above during the description of the mold 200.

In the next step of the method of the present invention, where the mold 400 is formed from a plurality of complementary mold portions, step 352 may be optionally employed to enhance a sealed condition of the closed surfaces of the mold 400, as before. This may be accomplished through the application of one or more sealing devices disposed upon one or more components of the mold 400. In step 354 of the method of the present invention, the mold 400 is inserted into an isostatic press. The isostatic press may preferably be a hot isostatic press and may preferably be of the type represented by the hot isostatic press 46 in FIG. 4 or the hot isostatic press 220 in FIG. 16. Alternatively, the step 354 may involve inserting the mold 400 into a cold isostatic press.

In the next step of the method of the present invention, the waste-binder mixture is processed in the mold 400 at step 356 to form a first product. This involves subjecting the waste-binder mixture to the pressure of a pressure fluid by introducing a pressure fluid selected from water, oils and inert gases. When a hot isostatic press treatment is used, the waste-binder mixture is preferably subjected to a temperature above the highest melting temperature of the thermoplastic material that will not degrade the other constituents. This may typically be from about 300° F. to about 600° F. The isostatic pressure treatment is also performed at pressures of from about 1,000 psi to about 40,000 psi.

Once processing of the waste-binder mixture is complete and the first product is formed, the mold 400 and first product are removed from the isostatic press. As shown in FIG. 19, further processing of the first product to achieve a substantially fully densified product or other product may take place by subjecting the first product to the process of the steps 362–368 while remaining within the mold 400. When this is desired, the mold 400 containing the first product should be of the type which may be subsequently substantially closed and processed as described below in connection with the steps 362–368.

When the first product is not subjected to the process of the steps 362–368 while remaining within fir mold 400, the first product is removed from the mold 400 according to step 358. This step may first include the removal of any sealing devices which may have been previously disposed upon one or more components of the mold 400. The first product is then removed from the mold 400. The first product may then, according to step 360, be subjected to the process of the steps 362–368 by inserting the first product into an open mold which is subsequently closeable for use with the process of those steps. Optionally, the first product may be inserted into or surrounded by an elastomeric bag, a foil bag, a foilized shrink tubing, polytetrafluoroethylene shrink tubing or polyvinyl chloride shrink tubing, in one piece or in the form of a multi-piece assembly, prior to being subjected to the process of the steps 362–368.

Figure 22:
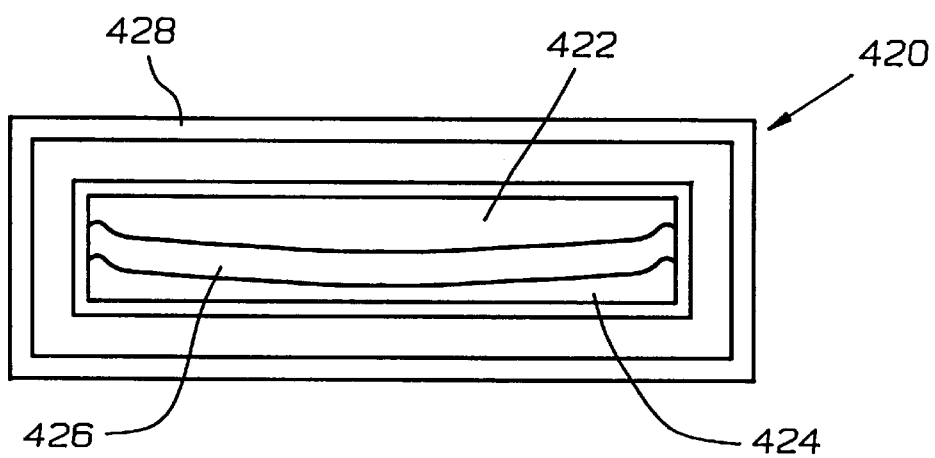
FIG. 22 is a top view of a mold used in accordance with a preferred embodiment of the present invention.

Referring again to FIG. 19, at step 350, the waste-binder mixture may, from the start, be alternatively introduced into another preferred type of mold suitable for use in the process of step 362–368. Referring now to FIG. 22, there is shown a top view of a second type of mold to be used with step 362–368. This mold, illustrated at 420, is shown to be a closed mold which, in this form, is capable for producing a stadium seat as the desired final product. The mold 420 is shown to include a first die 422 and second die 424 which are preferably complimentarily shaped so a to form a molding space 426 therebetween when the first die 422 and the second die 424 are brought together in a complementary relation. The first die 422 and the second die 424 may constructed of those materials set forth previously with regard to the mold 260 described in FIGS. 14 and 15. As before, the mold 420 may also preferably be substantially surrounded by a silicone or elastomeric sleeve 428 on its side and bottom surface. The mold 420 may also preferably include some or all of the features previously described in connection with the mold 260 or the mold 400. Therefore, these features will not be repeated here. Once the mold 420 is closed, a vacuum of at least approximately 27 inches Hg may be produced within the mold 420. This may be accomplished in a similar manner as before. In addition, additional waste-binder mixture may be introduced into an enclosure disposed in communication with the molding space 426.

At step 362 of the method of the present invention, the mold 420 is sealed as before. Where a first product contained within a mold 400 of the type previously described is subsequently subjected to the steps 362–368 to form a substantially completely densified second product as discussed above, the mold 400 is preferably also substantially sealed and evacuated at this time.

At step 364 of the method of the present invention, the mold 400, which is at this time a substantially sealed mold, or, alternatively, a substantially sealed version of the mold 400 from step 356, is inserted into an isostatic press. The preferred selection of isostatic press for this step is a hot isostatic press. The isostatic press may preferably be of the type previously described in connection with FIG. 4 or the hot isostatic press 220 described in connection with FIG. 16. Alternatively, it will be appreciated that other types of isostatic presses may be used. At step 366 of the method of the present invention, the waste-binder mixture is processed in the mold 420 to form a second product. The second product is distinguishable from the first product in that it is substantially completely densified, as compared to the partially densified first product formed by the steps 352–358. As before, a liquid or gas pressure/heat transfer medium is introduced into the isostatic press. The isostatic press is then operated in a similar manner as before to melt the waste-binder mixture and densify it this time to a substantially fully densified material. During this process, the temperature and pressure ranges and time periods are substantially as previously described. The pressure fluid used is selected from the group consisting of water, oils and inert gases.

In step 368 of the present invention, the second product is removed from the mold 420. This is accomplished by first removing the mold 420 from within the isostatic press, including removing any sealing enhancement devices which may have been previously applied to one or more portions of the mold 420, and then opening the mold 420.

As before, both the first product produced from steps 352–358 and the second product produced from steps 362–368 of the present invention may be useful articles. Optionally, the first product and/or the second product may be subjected to one or more types of post-pressing mechanical treatment as shown at step 170 in FIG. 19. These treatments may be of the types previously described. This process yields a consumer product represented at step 372.

Examples of useful articles made from the process of the present invention include those previously set forth. Products of the present invention may preferably have a consistency similar to that of wood in some respects. These products are expected to exhibit a yield stress of from about 500 psi to about 1500 psi, tensile stress of from about 1000 psi to about 2500 psi, and an elongation at failure of from about 7% to about 70%. These products are also expected to exhibit a modulus of elasticity of from about 10,000 psi to about 20,000 psi and an energy to break of from about 100 in-lb to about 1000 in-lb. One advantage of the present invention is the ability to make products having a cross-section of greater than about 2 inches which is the current limit using extrusion techniques on these types of materials. Other advantages include higher tensile strength and elongation, which result in a material of enhanced strength, greater deformation before breaking, enhanced screw retention and enhanced deflection at load over a span of the material. In addition, these and other properties of the materials made using the present invention can be varied by varying process conditions and the initial input material, such as by plastic to rubber ratio, or by other additives, including ultrahigh molecular weight polyethylene.

EXAMPLE 6

10 lbs. of reclaimed used automobile tires ground to 30 mesh particle size are mixed with 10 lbs. of ultrahigh molecular weight polyethylene of 16 mesh particle size and molecular weight of approximately 5 million. This mixture is then inserted into a mold that is transparent to microwave and radio frequency energy and is subjected to radio frequency heating in a microwave unit for approximately 7 minutes at a frequency of 2450 mHz and a power of 750 watts. The ultra high molecular weight polyethylene is of the type sold under the name Hifax 1900H by Himont USA of Wilmington, Del. The mold is cooled and a partially densified product is removed. The partially densified product is then enshrouded in a foilized bag, and sealed. This construct is then placed into a hot isostatic press, available from National Forge of Erie, Pa. The hot isostatic press is sealed and the partially densified product is subjected to a pressure of 9300 psi and a temperature of 385° F. for 4 hours. The mold is removed from the hot isostatic press and the resulting product is a substantially densified product in the shape of a board. The product is machined on its external surfaces to remove surface irregularities. The product is tested for its mechanical properties and the following results are obtained:

Average yield stress=770 psi±67 psi

Ultimate tensile stress=1406 psi±140 psi

% Elongation=47%±14%

Modulus of Elasticity=11,510±677 psi

Energy to Break=166 in-lb±68 in-lb

The present invention includes the use of an elastomeric mold as described above. The present invention thus contemplates a method for forming products, including biocompatible components, using an elastomeric mold. The steps of the method for forming biocompatible components using an elastomeric mold are substantially similar to the steps previously set forth. The formation of an elastomeric mold for accomplishing the formation of molded products will now be described with reference to FIGS. 23–32.

Figure 23:
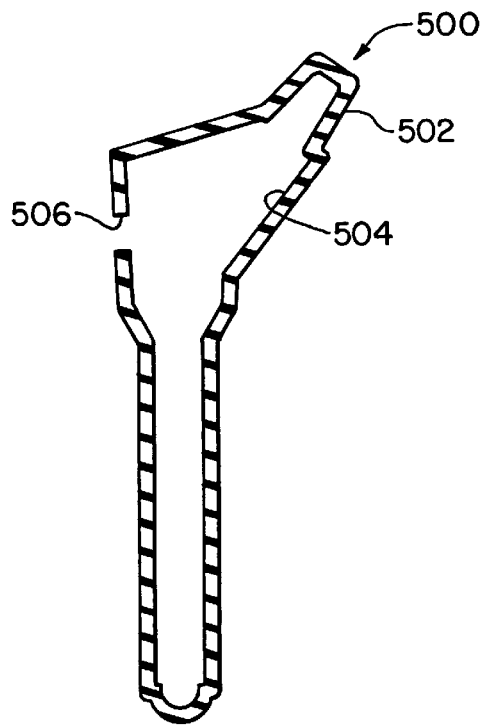
FIG. 23 is a cross-sectional view of an elastomeric mold having a drainage aperture according to a preferred embodiment of the present invention.

According to another preferred embodiment of the present invention, there is provided an apparatus and method for forming biocompatible components as illustrated in FIGS. 23–32. With reference now to FIG. 23, there is shown a cross-sectional view of an elastomeric mold at 500. The elastomeric mold 500 is preferably formed to be of a specific size and a specific configuration corresponding to the final desired configuration of a component formed by the present process, such as a biocompatible component, but of larger dimensions. It will be appreciated, however, that the elastomeric mold 500 may be of any suitable shape for accomplishing a molding of any desired shape of component. As such, it is operable to contain a material suitable for pressing during a compression process. The elastomeric mold 500 is shown to include an outer surface 502 which may preferably be of a generally smooth surface configuration. The elastomeric mold 500 is also shown to include an inner surface 504 whose configuration and surface texture substantially correspond to the final desired configuration and surface texture of the exterior surface of a component formed through this process. The dimensions of the inner surface 504 are preferably precisely scaled to be larger than the final desired dimensions of the biocompatible component by a preselected amount. This preselected amount is preferably substantially equal to the predicted ratio of compression of the material being used to form the molded component so that the compression of the material from which the component is formed will result in a product of desired final dimensions. Where applicable, the dimensions of the inner surface 504 may also be varied to compensate for any variations in compression due to the presence of the elastomeric mold 500 itself.

The elastomeric mold 500 is preferably made from a material which may be coated upon a mandrel in liquid form and subsequently converted to an elastomeric material, either thermally, chemically, through the application of pressure, through evaporation of one or more components of the liquid material, through any combination of the above, or through any other suitable means. Suitable materials include those selected from the group consisting of silicone rubbers, urethanes, fluoroelastomers and vulcanized latex. It will be appreciated, however, that any suitable elastomeric material may be used, provided that the material is suitable for withstanding the temperature and pressure conditions and the chemical exposure discussed herein, and exhibits suitable compression characteristics. Due to the nature of the elastomeric material used for constructing the elastomeric mold 500, the configuration, dimensions and surface and texture of the outer surface 502 may also substantially correspond to the configuration, dimensions and surface texture of the inner surface 504, albeit perhaps in a lesser defined manner.

The elastomeric mold 500 is preferably made of a material that is reusable over several iterations of the process discussed herein. Optionally, the elastomeric mold 500 may be constructed of a material that is inexpensive to produce and is thus disposable or recyclable following a single use. A desirable quality of the material used for constructing the elastomeric mold 500 is that it is resistant to degradation or damage due to exposure to the thermochemical and pressure conditions which occur during this process. The elastomeric mold material is also preferably able to be pierced or cut in a limited fashion without undergoing substantial dimensional change, and also without experiencing additional undesired tearing of the material resulting therefrom. In addition, the elastomeric mold material is preferably able to be separated from the mandrel material from which it is formed without damage to or change in dimension of the mold. The elastomeric mold 500 is able to be stretched well beyond its usual dimensions when substantially no forces are applied to it. For example, one elastomer material used for the elastomeric mold 500 is able to stretch to 300 percent of its usual size.

The thickness of material from which the elastomeric mold 500 is made is preferably from about one-eighth inch to about one-fourth inch, although it will be appreciated that other suitable thicknesses may be used. Generally, for the forming of larger components whose smallest dimension is on the order of approximately three inches, the thickness of the material is closer to one-fourth inch. For smaller components whose smallest dimension is less than three inches, the thickness of material may be closer to one-eighth inch. Typically, the thickness of material is reduced for smaller components and for components having more detailed surface textures in order to enhance the ability of the elastomeric mold 500 to transfer desired surface contours and texture features to the product being formed. It will also be appreciated that the thickness of material used for forming the elastomeric mold 500 may vary over the surface of the mold, especially where necessary to create the detail of certain surface contours and texture features upon the external surface of the component being formed.

The elastomeric mold 500 also preferably includes at least one aperture made during formation of the mold or created thereafter. Such an aperture is able to facilitate removal of a mandrel or a mandrel material from within the elastomeric mold 500 once the elastomeric mold 500 is formed. As shown in FIG. 23, such an aperture may be provided as a drainage aperture 506. The drainage aperture 506 is able to remove a mandrel material, such as wax, that has been converted to a liquid state for drainage from within the elastomeric mold 500. This process will be described in further detail below. The drainage aperture 506 is able to provide means for filling the elastomeric mold 500 with a compressible material as will also be described below. The drainage aperture 506 may be sealed by a plug, or other removable closure. This arrangement is shown and described below.

Figure 24:
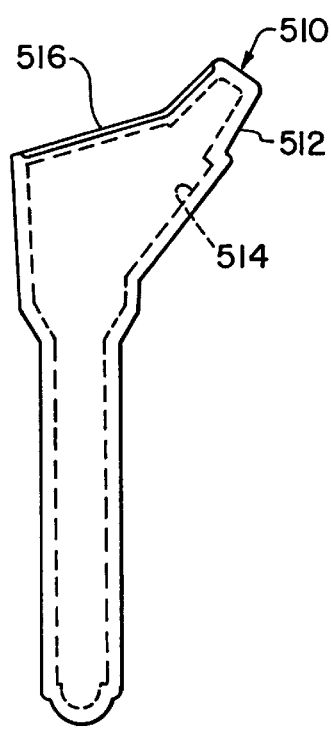
FIG. 24 is a perspective view of an elastomeric mold with an elongated aperture disposed on a surface thereof according to a preferred embodiment of the present invention.

Referring now to FIG. 24, there is shown a perspective view of an elastomeric mold at 510. The elastomeric mold 510 is of substantially the same construction as the elastomeric mold 500 shown previously in FIG. 23. In this regard, the elastomeric mold 510 includes an outer surface 512 and an inner surface 514. The elastomeric mold 510 is shown to include an aperture in the form of an elongated aperture 516 disposed along a surface of the elastomeric mold 510. The elongated aperture 516 may be made during formation of the mold or created thereafter by cutting or otherwise deforming the mold material in a controlled manner following formation. In one embodiment, the elongated aperture 516 may be sealed condition by a method well known to those skilled in the art. Examples of methods for sealing the elongated aperture 516 include heat sealing, application of suitable adhesives and application of an external sealing device. In another embodiment, the elongated aperture 516 is left unclosed because suitable enclosure is achieved when the elastomeric mold 510 is sealed within another enclosure, such as a foilized bag, prior to pressing. It will be appreciated, however, that any suitable sealing method may be employed.

The elongated aperture 516 is preferably of a sufficient size so that the elastomeric mold 510 may be stretched around the mandrel located therewithin following formation of the mold, while being large enough to accomplish the removal procedure without undue stretching of the mold material where the elastomeric mold 510 is unable to return to its original configuration. This allows the elastomeric mold 510 to be reused. The elongated aperture 516 may of any suitable configuration, although a preferred configuration is one that is conveniently operable to be substantially sealed by such means as described above.

Figure 25:
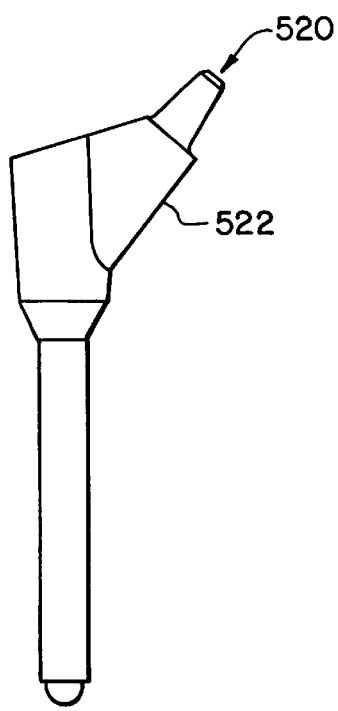
FIG. 25 is a perspective view of a mandrel used for forming an elastomeric mold according to a preferred embodiment of the present invention.

Referring now to FIG. 25, there is shown a perspective view of a mandrel 520 which is shown to include an outer surface 522. The mandrel 520 is preferably constructed of a material suitable for withstanding a pressing operation, and suitable for transferring the desired configuration and surface detail to an elastomeric mold made therefrom. Suitable materials include metals, such as aluminum, and materials which may subsequently be converted to a liquid state for removal from the elastomeric mold following formation, such as wax. Other suitable materials may also be used.

The configuration and surface texture of the outer surface 522 of the mandrel 520 preferably substantially corresponds to the intended final configuration and surface texture of the component to be formed from the mandrel 520. The dimensions of the mandrel 520 and the surface texture features on the outer surface 522 will be larger than the final desired dimensions of the component formed by this process, and its surface texture features, by a ratio equal to the predicted compression of the material from which the component is made. As such, the mandrel 520 is preferably a scaled-up model of the component being formed. The relative ratios of dimensions between particular surface features are therefore preferably substantially the same ratios along the outer surface 522 as is desired for the final product. The configuration of the mandrel 520, including any features that are located on the outer surface 522, are created in reverse in the elastomeric mold. In turn, these features are transferred in reverse from the mold so that they appear in the desired arrangement in the biocompatible component being molded by this process, including those on its external surface. Alternatively, the mandrel 520 may include one or more projections (not shown) which are suitable for forming certain surface features, such as the drainage aperture 506 shown in FIG. 23, or other features.

The method of this aspect of the present invention will now be described with reference to FIGS. 25–32. The method is described in connection with forming a biocompatible hip component, although it will be appreciated that this method may be used to form other types of products. In the first step of this method, an elastomeric mold suitable for containing a material suitable for pressing during a compression process, such as that shown at 500 in FIG. 23 or at 510 in FIG. 24, is provided. In a preferred method, the elastomeric mold is formed by dip-forming about a mandrel, such as that shown at 520 in FIG. 25. Alternatively, other methods for forming an elastomeric mold may be utilized. A mandrel 520 may be prepared by means well known to those skilled in the art from a material of the selections set forth above.

The step of forming an elastomeric mold from the mandrel 520 comprises coating the mandrel 520 with a liquid material which is able to be subsequently converted to an elastomeric material by any of the means described above. In one arrangement, this step comprises providing a bath of such a liquid material (not shown). The mandrel 520 may then preferably be coated with the liquid material by dipping the mandrel 520 into the liquid material bath. The mandrel 520 preferably remains in the liquid material bath for a time suitable for the particular liquid material selected to coat the desired portion of the outer surface 522 of the mandrel 520. The mandrel 520 may be immersed so that the liquid material coats the entire outer surface 522 or only a portion thereof. Preferably, the time over which the mandrel 520 is immersed in the liquid material bath is sufficient to provide the desired thickness or thicknesses of coating, either in uniform or varied thicknesses, as may be desired for the creation of certain surface features. The mandrel 520 may also be manipulated in any manner suitable for achieving the desired coating distribution. This may include rotation of the mandrel 520 within the liquid material bath, selected draining of liquid material from one or more portions of the mandrel 520, or iterative application of the mandrel 520 to the liquid material bath, either in whole or in part.

Alternatively, it will be appreciated that the step of coating the mandrel 520 with a liquid material may be accomplished by or may include other coating procedures. For example, the mandrel 520 may be manually coated either in whole or in part, and perhaps in addition to the above procedure. Such methods may include brushing, spraying or otherwise exposing the mandrel 520 to the liquid material in any way effective for accomplishing the desired distribution of liquid material upon the mandrel 520.

It will be appreciated that in some circumstances, it may be desirable to provide non-uniform thicknesses for various reasons pertinent to the subsequent molding process. For example, in some situations, it may be desirable to provide a thinner coating over a specific area of the mandrel 520 because the specific area may involve detailed surface texture features which are more easily transferred to the product being molded through a thinner elastomeric mold. It will also be appreciated that in some circumstances, it may be desirable to form a coating over only a portion of the mandrel 520. In these circumstances, the mandrel 520 may only be partially dipped in a liquid material bath or may receive lesser liquid material through spraying.

Once the liquid material has been applied to the mandrel 520 and/or while any desired manipulations and/or iterations of the above steps have been made, the liquid material which remains as a coating on the mandrel 520 is converted to an elastomeric material. This may be accomplished by removing the mandrel 520 completely from exposure to the liquid material, which in one circumstance includes the step of removing the mandrel 520 from the liquid material bath. The step of converting the liquid material to an elastomeric material is accomplished either thermally, chemically, through the application of pressure, through evaporation of one or more components of the liquid material, through any combination of the above, or through any other suitable means. Most preferably, this is accomplished by allowing the liquid material to dry, which involves an evaporation of one or more components of the liquid material. Examples of alternative methods include allowing the liquid material to cool or undergo another suitable change in thermochemical state.

Figure 26:
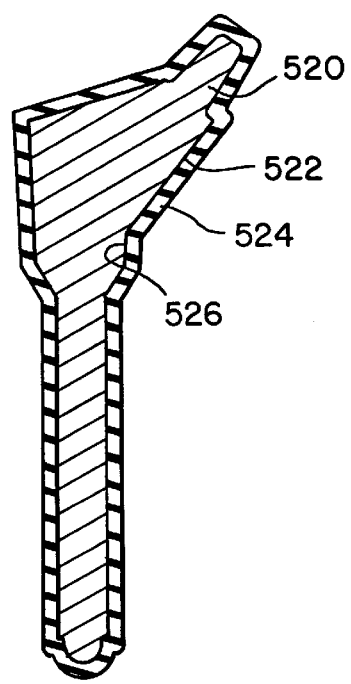
FIG. 26 is a cross-sectional view of a mandrel with an elastomeric mold disposed thereupon, according to a preferred embodiment of the present invention.

Referring now to FIG. 26, once the liquid material has been converted to an elastomeric material as described above, the mandrel 520 has an elastomeric material in the form of an elastomeric mold 524 disposed upon its outer surface 522. The elastomeric mold 524 may preferably be substantially similar to that shown at 500 or 510 in FIGS. 23 and 24. The elastomeric mold 524 includes an inner surface 526 that is preferably configured and defined in sufficient surface contour and texture detail as may be desired on the product formed using the elastomeric mold. Preferably, the process by which the elastomeric mold 524 is made is sufficient to transfer the definition of surface detail down to one-fifteen thousandth of an inch to the inner surface 526 of the elastomeric mold 524.

In the next step of the present invention, the elastomeric mold 524 is removed from the mandrel 520. In the case where the mandrel 520 is composed of a material which can be converted to a liquid state such as wax, the elastomeric mold is preferably of the form shown at 500 in FIG. 23. The material from which the mandrel 520 is made is then converted to the liquid state, such as by heating, and drained through the drainage aperture 506. Where no aperture is created prior to the formation of the elastomeric material, a drainage aperture may be created following formation of the elastomeric mold by cutting or otherwise deforming the elastomeric mold material in a controlled manner. Any such drainage aperture is preferably created to the smallest sufficient size that is suitable for draining the mandrel material from within the elastomeric mold, once the mandrel material is converted to the liquid state.

In the case where the mandrel 520 is made from a metal or other material not suitable for being converted to the liquid state as described above, an elongated aperture, such as that shown at 516 in connection with FIG. 24, is preferred for removing the elastomeric mold from the mandrel 520. The elongated aperture 516 may be formed during the formation of the elastomeric mold, or may alternatively be created following formation of the elastomeric mold by cutting or otherwise deforming the elastomeric material in a controlled manner. The elastomeric mold 510 is then stretched so that it may be removed from upon the mandrel 520. Using any of the above methods, the removal of the elastomeric mold from upon the mandrel yields an elastomeric mold of the type illustrated as 500 in FIG. 23 or 510 in FIG. 24.

Figure 27:
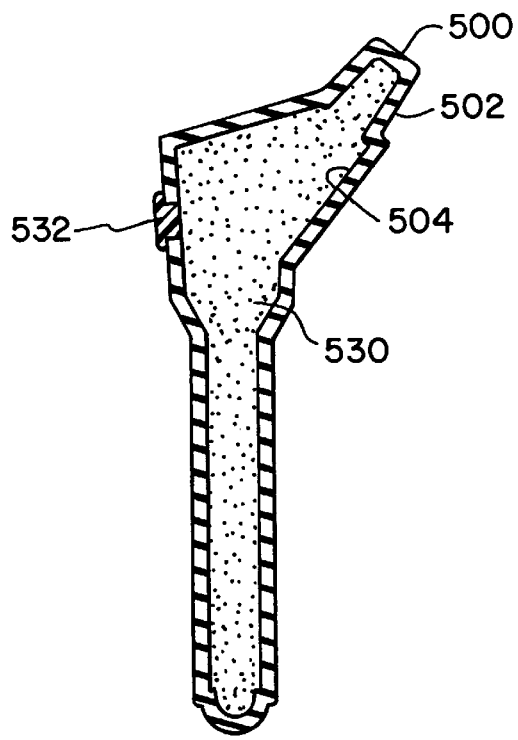
FIG. 27 is a cross-sectional view of an elastomeric mold having an drainage aperture and plug, which is filled by a material suitable for pressing according to a preferred embodiment of the present invention.
Figure 28:
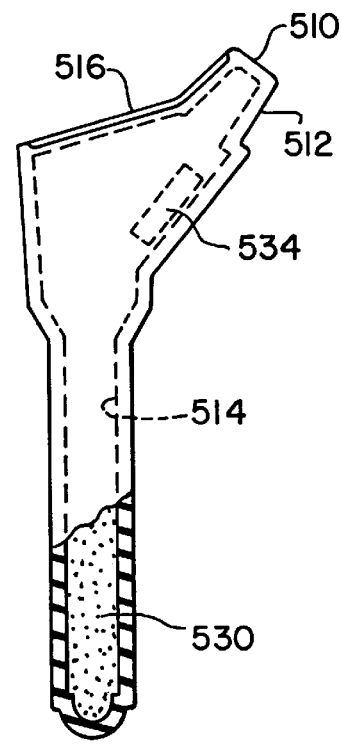
FIG. 28 is a partial cutaway view of an elastomeric mold with a seam disposed thereon, and enclosing a material suitable for pressing according to a preferred embodiment of the present invention.

In the next step of the method of the present invention, a material suitable for pressing is introduced into the elastomeric mold 500 or 510. Referring now to FIGS. 27 and 28, a material suitable for pressing, such as a molding powder 530 of the types previously discussed herein, is inserted into the elastomeric mold through an aperture such as drainage aperture 506 or elongated aperture 516. The amount of powder inserted into the elastomeric mold 500 or 510 will depend upon the elastic properties of the mold, the compressibility of the powder inserted therein, the compression conditions and the size and configuration of the particular product being formed. Typically, the molding powder 530 is inserted into the elastomeric mold so as to substantially fill the mold, and the elastomeric mold is then enhanced in a substantially sealed condition. This may be accomplished by any suitable mechanical sealing means. Alternatively, the elastomeric mold and powder may be enclosed by a second container, such as a foilized bag, which is subsequently sealed.

In the case where the elastomeric mold is of the configuration shown as 500 in FIG. 23, the elastomeric mold 500 may preferably be enhanced in a substantially sealed condition through the use of an appropriate closure for the drainage aperture 506 such as the plug 532 shown in FIG. 27. It will be appreciated, however, that under some circumstances, the drainage aperture 506 may remain open during the compression process. In addition, the closure may take on other forms besides the plug 532 which are suitable for enhancing a substantially sealed condition of the elastomeric mold 500.

In the arrangement where the elastomeric mold includes an elongated aperture 516 as in FIG. 24, the elongated aperture 516 may preferably be sealed through the use of an appropriate sealing means. This may be accomplished through a closure of the elongated aperture 516 itself, through one or more adhesives or through one or more external sealing devices applied to the elongated aperture 516. These may be designed to pull the opposing surfaces of the elongated aperture 516 together in a contacting or overlapping relation to form a seam. One example of a method through which the elongated aperture 516 may be enhanced in a substantially sealed condition is by bringing two opposing surfaces of the elongated aperture in a substantially aligned relation and heat sealing the opposing surfaces together. Alternatively, it will be appreciated that the elongated aperture 516 may remain unsealed during the compression process. This configuration is shown in FIG. 28.

Figure 29:
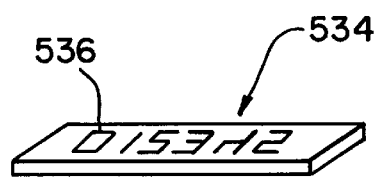
FIG. 29 is a perspective view of a die insert according to a preferred embodiment of the present invention.

To provide means for causing certain surface features to be created upon the exterior surface of the product being formed, the elastomeric mold 510 may include a die insert 534 as shown in FIG. 29. The die insert 534 is preferably made of a suitable material for remaining in a substantially static integrity throughout the molding process, and is suitable for transferring certain features to a product being molded. The die insert 534 may accordingly have certain alphanumeric indicia or other textural features, such as those shown at 536 in FIG. 29, imprinted in reverse on its surface so that these features become transferred to the product being formed. The die insert 534 may preferably be inserted into an elastomeric mold through any suitably sized aperture, and positioned upon an interior surface thereof. As shown in FIG. 28, a die insert 534 is positioned upon the inner surface 514 of the elastomeric mold 510. The die insert 534 may be positioned at any desired location, and may be enhanced in a secured position upon the inner surface 514 by any suitable means, such as a small amount of adhesive. The die insert 534 is preferably positioned as desired prior to introducing the molding powder into the elastomeric mold.

In the next step of the present invention, a material suitable for pressing, such as the molding powder 530, is subjected to a cold isostatic pressure treatment. The cold isostatic pressure treatment is accomplished by inserting the elastomeric mold 500 or 510 containing the material to be pressed into the cold isostatic press such as that shown at 32 in FIG. 2. In this step of the present invention, the elastomeric mold 500 or 510 will effectively take the place of the first container 98 shown in FIG. 2. The cold isostatic pressure treatment is then applied in similar manner as before.

Figure 30:
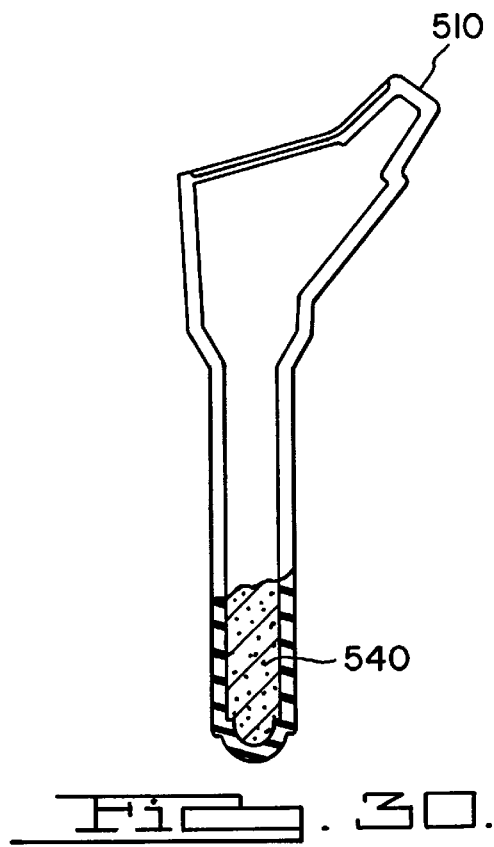
FIG. 30 is a partial cutaway view of an incompletely consolidated stock surrounded by an elastomeric mold according to a preferred embodiment of the present invention.

The cold isostatic pressure treatment is operable to form an incompletely consolidated stock whose compression characteristics are described previously. In this process, the incompletely consolidated stock is shaped to roughly correspond to the desired final shape of the product being formed. Referring now to FIG. 30, there is shown the elastomeric mold 510 from FIG. 28 which now contains an incompletely consolidated stock 540. In the condition following the cold isostatic pressure treatment, the elastomeric mold 510, and the now pressed material contained therein, are of reduced size compared to the size prior to the cold isostatic press treatment. At this stage, the elastomeric mold 510 is shown to substantially surround an incompletely consolidated stock 540 which has been formed from the material suitable for pressing such as the powder 530. It will be appreciated that the elastomeric mold 510 shown in connection with FIG. 30 may at this stage also be similar to the elastomeric mold 500 shown in FIG. 27.

According to the next step of the present invention, the incompletely consolidated stock 540 may optionally be removed from within the elastomeric mold. In some cases, it may be desirable to keep the incompletely consolidated stock 540 within the elastomeric mold for further processing. Where the elastomeric mold is of the configuration shown at 500 in FIGS. 23 and 27, the elastomeric mold 500 may be suitably cut or deformed to remove the incompletely consolidated stock. Where the elastomeric mold is of the configuration shown at 510 in FIGS. 24 and 28, the elastomeric mold 510 may be removed in a way that allows for its reuse. This may be accomplished by opening the elongated aperture 516, if it has been previously closed or sealed, and utilizing the elastic properties of the elastomeric mold 510 to remove the mold from its position surrounding the incompletely consolidated stock 540. This involves a stretching of the elastomeric mold 510 to the degree that the incompletely consolidated stock 540 may fit through the stretched elongated aperture 516. The incompletely consolidated stock 540 may be suitable for use as an end product. It will therefore be appreciated that the cold isostatic pressure treatment may optionally be the only isostatic pressure treatment used.

In the next step of a preferred method of the present invention, the incompletely consolidated stock 540 is subjected to a hot isostatic pressure treatment. The hot isostatic pressure treatment may optionally be the only isostatic pressure treatment used. To prepare the incompletely consolidated stock 540 for the hot isostatic pressure treatment, it is first preferably placed into a second container. The second container may preferably be of the type shown in FIG. 5 at 108, but may alternatively be of any type suitable for maintaining integrity and resisting thermal and pressure degradation during the hot isostatic pressure treatment. Optionally, the elastomeric mold 510 may remain upon the incompletely consolidated stock 540 during the hot isostatic pressure treatment. In this arrangement of the process, the same elastomeric mold 510 may be utilized for both the cold isostatic pressure treatment and the hot isostatic pressure treatment. The second container 108, and the elastomeric mold 510, if applicable, containing the incompletely consolidated stock 540 is then inserted into a hot isostatic pressure vessel such as that shown at 46 in FIG. 4. The incompletely consolidated stock 540 is then subjected to a hot isostatic pressure treatment in similar manner to that previously described. This process is operable to form a product having substantially final configuration, dimensions and surface texture.

Figure 31:
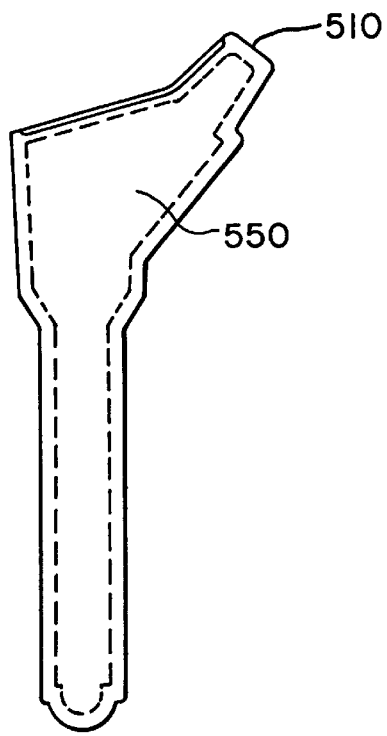
FIG. 31 is a perspective view of a pressed biocompatible component surrounded by an elastomeric mold, according to a preferred embodiment of the present invention.

The hot isostatic pressure treatment is preferably operable to convert the incompletely consolidated stock 540 to a substantially consolidated product. Upon conclusion of the hot isostatic pressure treatment, the second container, which substantially surrounds the substantially consolidated product in a compressed condition, is removed from within the hot isostatic pressure vessel 46. The second container is then removed from the substantially consolidated product by any suitable method. Where the elastomeric mold 510 has been used for the hot isostatic pressure treatment, the resulting arrangement is substantially as shown in FIG. 31, with the elastomeric mold 510 surrounding the substantially consolidated product 550.

Figure 32:
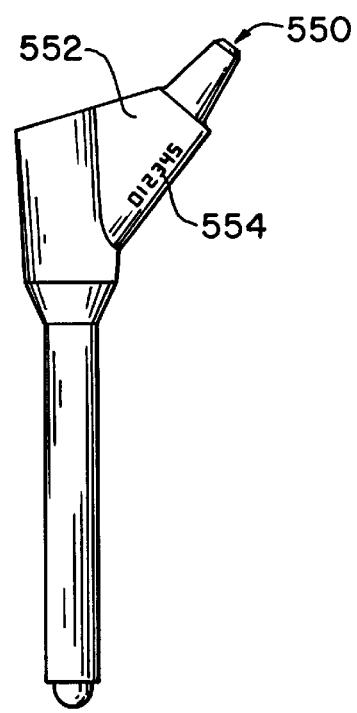
FIG. 32 is a perspective view of a biocompatible component formed according to a preferred embodiment of the present invention.

The substantially consolidated product 550 may then be removed from the elastomeric mold 510 yielding a substantially consolidated product 550 as shown in FIG. 32. Referring now to FIG. 32, there is shown a substantially consolidated product 550 in the form of a biocompatible hip component as formed by the process of the present invention. The substantially consolidated product 550 is shown to include an outer surface 552 upon which one or more surface texture features may be transferred from both the optional die insert 534 and the elastomeric mold 510. The substantially consolidated product 550 is preferably of substantially final configuration, dimensions and surface texture following the hot isostatic pressure treatment. It will be appreciated, however, that minor surface variations or inconsistencies may be removed from the surface of the substantially consolidated product 550 through a subsequent milling or other suitable treatment process.

In another aspect of the present invention, there is provided a method for making a molding sleeve suitable for processing the various products described herein. The molding sleeve produced by this method is most preferably used in a hot isostatic press procedure for enhancing the surface features of a thermoplastic product being molded through the method described above. It will be appreciated that this molding sleeve may be used in other steps of the method of the present invention, and in other processing methods as well.

Figure 33:
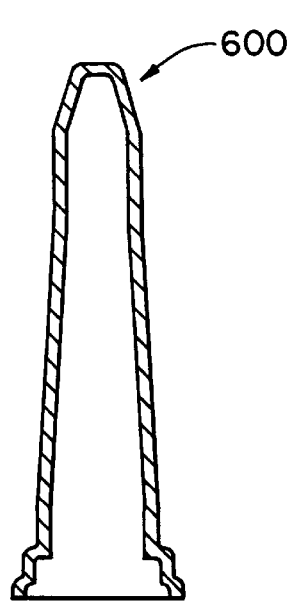
FIG. 33 is a cross-sectional view of a sleeve formed according to a preferred embodiment of the present invention.
Figure 34:
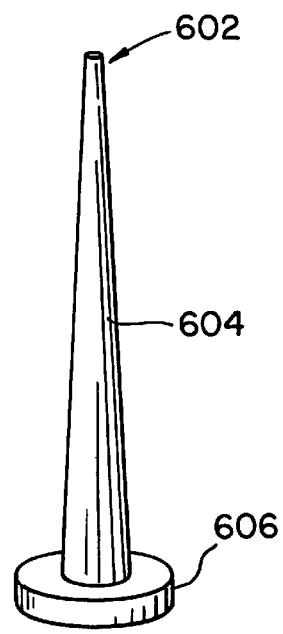
FIG. 34 is a perspective view of a mandrel used for forming a sleeve according to a preferred embodiment of the present invention.

The method for making a molding sleeve will now be described with reference to FIGS. 33–37. Referring now to FIG. 33, there is shown a molding sleeve, generally at 600. The molding sleeve 600 is preferably constructed of an elastomeric material, and may be of similar form to the elastomeric mold 500 or 510 previously described. Suitable materials for the molding sleeve 600 include silicone rubbers, high temperature urethanes, fluoroelastomers and vulcanized latex. Referring now to FIG. 34, there is shown a mandrel at 602. According to this aspect of the method of the present invention, a mandrel is a preferred tool used in the process for making the molding sleeve 600. The mandrel 602 is shown to include a main body 604 that is able to provide an interior surface to a product being formed as a template for the molding sleeve 600. The mandrel 602 also includes a base 606, which is able to enclose a molding space external to the main body 604, within which a molding material, such as a molding powder, may be contained. The mandrel 602 is preferably made of aluminum or other suitable metal, although it will be appreciated that any suitable material may be used.

Referring now to FIG. 35, there is shown a cold isostatic press unit at 608. The cold isostatic press tool 608 includes a main body 610 which is able to create a molding enclosure within which a molding material, such as a molding powder, may be contained. The cold isostatic press tool 608 also includes a base 612 which is operable for cooperating with the base 606 of the mandrel 602 for substantially completing a molding enclosure. The cold isostatic press tool 608 is also shown to include a plurality of vacuum ports 614 and 616 which are used to substantially evacuate the atmosphere within the cold isostatic press tool 608 from the molding material located therewithin. In this step of the method of the present invention, the mandrel 602 is inserted into the cold isostatic press tool 608 and the remainder of the interior of the cold isostatic press tool 608 is filled substantially with a molding material such as molding powder 618. The mandrel 602 is then inserted completely within the cold isostatic press tool 608 so that the base 606 of the mandrel 602 is substantially flush with the base 612 of the cold isostatic press tool 608. The base 606 of the mandrel 602 is then preferably secured in a substantially secured relation within the base 612 of the cold isostatic press tool 608 by any suitable means. One example of a suitable means is a clamp 620 which is operable to substantially surround the base 612 circumferentially. The above steps may preferably be performed with the cold isostatic press tool 608 in an inverted orientation. Once the mandrel 602 has been substantially secured within the cold isostatic press tool 608, the atmosphere within the cold isostatic press tool 608 is substantially evacuated through the vacuum ports 614 and 616. The cold isostatic press tool 608 is then placed within a cold isostatic pressure vessel, which may be of the type previously described. The cold isostatic pressure vessel is then operated at pressures ranging from about 700 psi to about 60,000 psi for approximately 0 minutes (no hold time) to about 15 minutes. This process forms ILO a molded product 630 which is shown in FIG. 36. The molded product 630 is a partially densified product whose densification characteristics are substantially similar to those previously described in connection with cold isostatic pressure treatments.

The molded product 630 is operable for being used as a template for the formation of the molding sleeve 600. In the next step of the method of the present invention, a material operable for being converted to an elastomeric material is applied to the external surface of the molded product 630. The application can be accomplished by brushing, spraying or any other suitable method. It will be recognized that any suitable number of iterations for applying this material may be used. The material applied to the external surface of the molded product 630 is preferably in a substantially liquid form when applied, and is converted to an elastomeric form upon drying, heating or other thermochemical change. In a preferred embodiment, the liquid material being applied to the molded product 630 is operable to dry to yield an elastomeric material in approximately 2 days. This may vary, however, depending upon the type of material used, the method of application used, the number of layers over which the material is applied and the desired final thickness of the elastomeric material.

Once the material is converted to an elastomeric material, it is in the form of a molding sleeve 600 disposed upon the molded product 630 as shown in FIG. 37. The molding sleeve 600 may then be removed from upon the molded product 630 for subsequent use. The molded product 630 may, in essence, be considered a sacrificial molded product in that it may serve the single purpose of providing a template for formation of the molding sleeve 600. Alternatively, the molded product 630 may be used for any other suitable use and may be a part of the molding process previously described. It will also be appreciated that the use of a mandrel is a preferred, but not required, method suitable for making the molded product 630 since some products can be molded isostatically without a mandrel.

In the next step of the method of the present invention, the molding sleeve 600 is utilized to enhance the external surface characteristics of a product being molded in accordance with the present invention. Preferably, the molding sleeve 600 is used in connection with an incompletely consolidated product, such as that shown at 540 in FIG. 30. The elastomeric mold, such as 510, is removed from upon the incompletely consolidated stock 540. The incompletely consolidated stock 540 is then substantially enshrouded by a molding sleeve manufactured according to the method set forth above that has been pre-manufactured to a substantially similar shape. It will be appreciated that the variety of shapes shown herein with respect to the incompletely consolidated stock 540 and the molding sleeve 600 are intended to show the varieties of shapes contemplated by the present invention. Once the molding sleeve 600 is disposed upon an incompletely consolidated stock of similar shape, the incompletely consolidated stock and molding sleeve 600 are preferably enclosed within a foilized bag and are processed in an isostatic pressure treatment. Preferably, the incompletely consolidated stock and molding sleeve 600 are processed in a hot isostatic pressure treatment in the same manner as previously described. Use of the molding sleeve 600 enhances the surface characteristics of the product being molded while it is pressed from a partially densified condition to a substantially densified condition. The enhancement of surface characteristics results at least in part from the ability of the elastomeric material to distribute the forces of a pressurized condition in a more even manner than can enclosures of other materials, such as foilized bags. After the pressing treatment, the molding sleeve 600 is removed to yield a substantially densified product having enhanced surface characteristics. These enhanced surface characteristics include improved smoothness, lettering or part identification symbols. This method is suitable for use in the formation of biocompatible components, such as the hip component previously described. It will be appreciated, however, that this method may be suitable for other uses as well.

It will be appreciated that the foregoing description of the preferred embodiment of the invention is presented by way of illustration only and not by way of any limitation. For example, a preheating step may be used to preheat the incompletely consolidated stock prior to placing the incompletely consolidated stock in the hot isostatic press. In addition, the various containers may be of different sizes and of different materials. Furthermore, filters such as paper towels may be located within the various evacuation tubes. Various alternatives and modifications may be made to the illustrative embodiment without departing from the spirit and scope of the invention.

What is claimed is:

1. A method for forming an article from recyclable waste material comprising the steps of:

providing waste material, at least a portion of which is selected from the group consisting of thermoplastics, thermosets, elastomers and mixtures thereof;

providing a flexible mold, said flexible mold being suitable for containing said waste material during a compression process;

providing a binder material operable for binding said waste material;

mixing said waste material with said binder material in a preselected ratio of waste material to binder material thereby forming a waste-binder mixture;

placing said waste-binder mixture into said mold; and subjecting said waste-binder mixture to an isostatic pressure treatment, said isostatic pressure treatment being operable to compress said waste-binder mixture in three dimensions.

2. The method for forming an article from recyclable waste material according to claim 1, further comprising the step of converting at least a portion of said binder to a state suitable for binding said ground waste material, following said step of mixing said ground waste material with said binder material in a preselected ratio of ground waste material to binder material, thereby forming a waste-binder mixture.

3. The method for forming an article from recyclable waste material according to claim 1, wherein said binder is selected from the group consisting of ultra high molecular weight polyethylene, high density polyethylene, low density polyethylene, polyethylene terephthalate and thermoplastics.

4. The method for forming an article from recyclable waste material according to claim 1, wherein said preselected ratio of ground waste material to binder material by weight is from about 80:20 to about 20:80.

5. The method for forming an article from recyclable waste material according to claim 1, wherein said preselected ratio of ground waste material to binder material by weight is about 50:50.

6. The method for forming an article from recyclable waste material according to claim 1, wherein said step of subjecting said waste-binder mixture to an isostatic pressure treatment includes the step of subjecting said waste-binder mixture to a hot isostatic pressure treatment.

7. The method for forming an article from recyclable waste material according to claim 1, wherein said step of subjecting said waste-binder mixture to an isostatic pressure treatment comprises the steps of:

subjecting said waste-binder mixture to a cold isostatic pressure treatment; and subjecting said waste-binder mixture to a hot isostatic pressure treatment.

8. The method for forming an article from recyclable waste material according to claim 1, further comprising the additional step of adding to said waste-binder mixture at least one additive suitable for enhancing at least one property of said waste-binder mixture prior to placing said waste-binder mixture into said mold.

9. The method for forming an article from recyclable waste material according to claim 1, wherein said step of subjecting said waste-binder mixture to an isostatic pressure treatment includes the step of subjecting said waste-binder mixture to an isostatic pressure treatment at a pressure of from about 1000 psi to about 40,000 psi.

10. The method for forming an article from recyclable waste material according to claim 1, wherein said step of subjecting said waste-binder mixture to an isostatic pressure treatment forms an intermediate product, and wherein said method further includes the step of subjecting said intermediate product to a second isostatic pressure treatment.

11. A method for forming biocompatible components having substantially final configuration and dimensions, said method comprising the steps of:

providing a flexible mold able to contain a compressible material during a compression process;

introducing said compressible material into said flexible mold;

subjecting said compressible material and said flexible mold to a cold isostatic press treatment thereby forming an incompletely consolidated stock, said cold isostatic pressure treatment being operable to compress said compressible material in three dimensions; and subjecting said incompletely consolidated stock to a hot isostatic press treatment thereby forming a biocompatible component having the substantially final configuration and dimensions, said hot isostatic pressure treatment being operable to compress said incompletely consolidated stock in three dimensions.

12. The method according to claim 11 wherein said step of providing a flexible mold comprises:

providing a mandrel having a shape corresponding to a final desired shape of a biocompatible product; and forming a flexible mold from said mandrel.

13. The method according to claim 12 wherein said step of forming a flexible mold from said mandrel comprises:

coating said mandrel with a material operable for being converted to a flexible material;

converting said material to a flexible material; and removing said flexible material from said mandrel, thereby yielding a flexible mold.

14. The method according to claim 12 wherein said mandrel includes surface features desired on a surface of said biocompatible component following formation.

15. The method according to claim 11 further comprising the step of inserting a die insert into said flexible mold, following the step of providing a flexible mold, said die insert being operable for forming a desired surface feature on said biocompatible component.

16. A method for enhancing the surface characteristics of a molded thermoplastic component comprising the steps of:

forming an elastomeric mold;

placing said elastomeric mold upon a molded component; and subjecting said molded component and said elastomeric mold to a hot isostatic pressure treatment.

17. The method for enhancing the surface characteristics of molded components according to claim 16, wherein said step of forming an elastomeric mold comprises the steps of:

providing an isostatic pressure device;

introducing a material suitable for molding into said isostatic pressure device;

subjecting said material suitable for molding to an isostatic pressure treatment, thereby forming a molded component;

applying a material operable for being converted to an elastomeric material to a surface of said molded component;

converting said material to an elastomeric material; and removing said elastomeric material from said molded component, thereby yielding an elastomeric mold.

18. A method for molding a powder to form a biocompatible component, said method comprising the steps of:

placing said powder into a flexible container; and subjecting said flexible container to an isostatic pressure treatment so as to form said biocompatible component from said powder.

19. The method according to claim 18, wherein said step of placing said powder into a flexible container includes the steps of:

placing said powder into a container formed from at least one material selected from the group consisting of silicone rubbers, urethanes, fluoroelastomers and vulcanized latex;

enclosing said container with a plug; and evacuating and then sealing said container.

20. The method according to claim 18, wherein said step of subjecting said flexible container to an isostatic pressure treatment forms an incompletely consolidated product, and wherein said method further includes:

placing said incompletely consolidated product into a second flexible container; and subjecting said second flexible container to a hot isostatic pressure treatment so as to form a substantially completely consolidated component.

21. The method according to claim 20, wherein said step of placing said incompletely consolidated product into a second flexible container includes the step of forming said second flexible container to include a layer selected from the group consisting of foil, a vapor barrier, and a heat sealable layer.

22. The method according to claim 20, wherein said step of placing said incompletely consolidated product into a second flexible container includes the steps of:

substantially enclosing said second flexible container; and substantially evacuating said second flexible container.

23. The method according to claim 18, wherein said step of subjecting said flexible container to an isostatic pressure treatment includes subjecting said flexible container to a hot isostatic pressure treatment.

24. The method according to claim 18, wherein said step of subjecting said flexible container to an isostatic pressure treatment includes subjecting said flexible container to a cold isostatic pressure treatment.

25. The method according to claim 18, wherein said step of subjecting said flexible container to an isostatic pressure treatment includes the steps of:

subjecting said flexible container to a cold isostatic pressure treatment; and subjecting said flexible container to a hot isostatic pressure treatment.

26. The method according to claim 18, wherein said flexible container is a non-gas permeable container.

27. The method according to claim 18, wherein said flexible container is an elastomeric container.

28. The method according to claim 20, wherein said second flexible container is a non-gas permeable container.

29. The method according to claim 20, wherein said second flexible container is an elastomeric container.

* * * * *